(12) United States Patent
Andersson et al.

(10) Patent No.: US 12,220,335 B2
(45) Date of Patent: Feb. 11, 2025

(54) EXPANDABLE STENT AND A METHOD FOR PROMOTING A NATURAL INTRACRANIAL ANGIOGENESIS PROCESS, AND USE OF THE EXPANDABLE STENT IN THE METHOD FOR PROMOTING A NATURAL INTRACRANIAL ANGIOGENESIS PROCESS

(71) Applicant: CEROFLO LIMITED, Galway (IE)

(72) Inventors: Sven Tommy Andersson, Älvsjo Älvsjo (SE); Eamon Oliver Brady, County Galway (IE)

(73) Assignee: CEROFLO LIMITED, Galway (IE)

( * ) Notice: Subject to any disclaimer, the term of this patent is extended or adjusted under 35 U.S.C. 154(b) by 18 days.

(21) Appl. No.: 18/149,830

(22) Filed: Jan. 4, 2023

(65) Prior Publication Data

US 2023/0149192 A1    May 18, 2023

Related U.S. Application Data

(63) Continuation of application No. 17/199,156, filed on Mar. 11, 2021, which is a continuation of application (Continued)

(30) Foreign Application Priority Data

Nov. 3, 2017    (GB) ...................... 1718299

(51) Int. Cl.
*A61F 2/91*    (2013.01)
*A61F 2/94*    (2013.01)

(52) U.S. Cl.
CPC .................. *A61F 2/91* (2013.01); *A61F 2/94* (2013.01); *A61F 2210/0014* (2013.01); (Continued)

(58) Field of Classification Search
None
See application file for complete search history.

(56) References Cited

U.S. PATENT DOCUMENTS

| 4,733,665 A | 3/1988 | Palmaz |
| 5,102,417 A | 4/1992 | Palmaz |

(Continued)

FOREIGN PATENT DOCUMENTS

| CN | 204655192 U | 9/2015 |
| EP | 1255507 B1 | 10/2003 |

(Continued)

OTHER PUBLICATIONS

International Search Report for PCT/EP2018/080213, dated Feb. 12, 2019 (PCT/ISA/210).

(Continued)

*Primary Examiner* — Paul B Prebilic
(74) *Attorney, Agent, or Firm* — Bookoff McAndrews, PLLC

(57) ABSTRACT

An expandable stent to enhance the supply of blood to downstream tissue which is being supplied with blood through a diseased intracranial artery with a stenosis formed therein by plaque with a bore therethrough. The expandable stent includes first and second end portions and a central portion. The central portion is configured in the expanded state of the stent to contact the stenosis with the first and second end portions anchoring the stent in the artery.

31 Claims, 7 Drawing Sheets

Related U.S. Application Data

Figure 5:
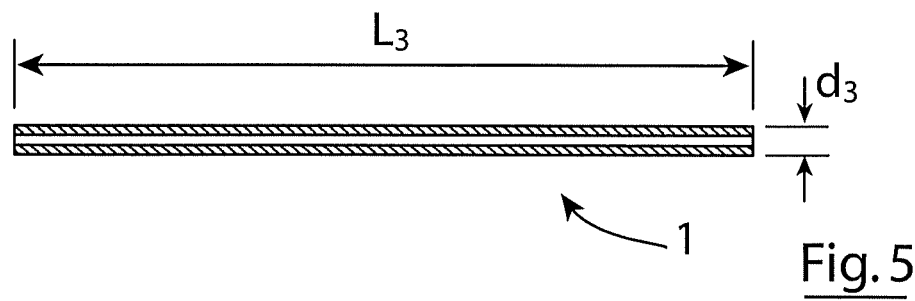

No. 16/760,919, filed as application No. PCT/EP2018/080213 on Nov. 5, 2018, now Pat. No. 11,819,430.

(52) U.S. Cl.
CPC . *A61F 2230/001* (2013.01); *A61F 2230/0067* (2013.01); *A61F 2250/0039* (2013.01); *A61F 2250/0098* (2013.01)

(56) References Cited

U.S. PATENT DOCUMENTS

| | | | |
|---|---|---|---|
| 5,725,572 | A | 3/1998 | Lam et al. |
| 5,741,327 | A | 4/1998 | Frantzen |
| 5,855,600 | A | 1/1999 | Alt |
| 5,861,027 | A | 1/1999 | Trapp |
| 5,922,021 | A | 7/1999 | Jang |
| 5,938,697 | A | 8/1999 | Killion et al. |
| 6,039,700 | A | 3/2000 | Sauter |
| 6,045,568 | A | 4/2000 | Igaki et al. |
| 6,190,406 | B1 | 2/2001 | Duerig et al. |
| 6,267,783 | B1 | 7/2001 | Letendre et al. |
| 6,273,910 | B1 | 8/2001 | Limon |
| 6,273,911 | B1 | 8/2001 | Cox et al. |
| 6,348,065 | B1 | 2/2002 | Brown et al. |
| 6,402,777 | B1 | 6/2002 | Globerman et al. |
| 6,409,754 | B1 | 6/2002 | Smith et al. |
| 6,585,758 | B1 | 7/2003 | Chouinard et al. |
| 6,652,579 | B1 | 11/2003 | Cox et al. |
| 6,911,016 | B2 | 6/2005 | Balzum et al. |
| 6,955,685 | B2 | 10/2005 | Escamilla et al. |
| 8,728,611 | B2 | 5/2014 | Becher et al. |
| 9,500,405 | B2 | 11/2016 | Hace et al. |
| 9,775,730 | B1 | 10/2017 | Walzman |
| 10,064,745 | B2 | 9/2018 | Hossainy et al. |
| 11,564,797 | B2 | 1/2023 | Chin et al. |
| 11,819,430 | B2 | 11/2023 | Andersson et al. |
| 2001/0044647 | A1 | 11/2001 | Pinchuk et al. |
| 2002/0052643 | A1 | 5/2002 | Wholey et al. |
| 2002/0052648 | A1 | 5/2002 | McGuckin et al. |
| 2002/0143384 | A1 | 10/2002 | Ozasa |
| 2003/0074049 | A1 | 4/2003 | Hoganson et al. |
| 2004/0015229 | A1 | 1/2004 | Fulkerson et al. |
| 2005/0038503 | A1 | 2/2005 | Greenhalgh et al. |
| 2005/0055082 | A1 | 3/2005 | Ben Muvhar et al. |
| 2005/0085923 | A1* | 4/2005 | Levine ................. A61F 5/0089 623/23.65 |
| 2005/0187609 | A1 | 8/2005 | Brar et al. |
| 2006/0184238 | A1* | 8/2006 | Kaufmann ............... D04C 1/06 623/1.53 |
| 2006/0229711 | A1* | 10/2006 | Yan ........................ A61F 2/82 623/1.38 |
| 2007/0005122 | A1 | 1/2007 | Inoue |
| 2007/0179590 | A1 | 8/2007 | Lu et al. |
| 2008/0132988 | A1 | 6/2008 | Jordan |
| 2010/0161033 | A1 | 6/2010 | Jantzen et al. |
| 2012/0083871 | A1 | 4/2012 | Ryan |
| 2012/0310363 | A1 | 12/2012 | Gill et al. |
| 2012/0323305 | A1* | 12/2012 | Benary ..................... A61F 2/07 623/1.15 |
| 2013/0138219 | A1 | 5/2013 | Toomey et al. |
| 2014/0243950 | A1 | 8/2014 | Weiner |
| 2014/0330305 | A1 | 11/2014 | Rood et al. |
| 2014/0350658 | A1 | 11/2014 | Benary et al. |
| 2015/0265438 | A1 | 9/2015 | Hossainy et al. |
| 2020/0254228 | A1 | 8/2020 | Taft et al. |
| 2021/0007869 | A1 | 1/2021 | Crawford et al. |
| 2021/0196488 | A1 | 7/2021 | Andersson et al. |
| 2023/0149192 | A1 | 5/2023 | Andersson et al. |
| 2023/0165586 | A1 | 6/2023 | Ben-Muvhar et al. |
| 2023/0225866 | A1 | 7/2023 | Chin et al. |
| 2023/0355413 | A1 | 11/2023 | Garrison et al. |

FOREIGN PATENT DOCUMENTS

| | | |
|---|---|---|
| EP | 1 666 003 A1 | 6/2006 |
| EP | 1488763 B1 | 11/2007 |
| EP | 1362564 B1 | 11/2008 |
| EP | 2 596 762 A1 | 5/2013 |
| EP | 3476370 B1 | 2/2023 |
| JP | 2003-527924 A | 9/2003 |
| JP | 2010-094510 A | 4/2010 |
| WO | 9716113 A1 | 5/1997 |
| WO | 9930643 A1 | 6/1999 |
| WO | WO 03/028522 A2 | 4/2003 |
| WO | 03101343 A1 | 12/2003 |
| WO | 2006108065 A2 | 10/2006 |
| WO | 2006127765 A1 | 11/2006 |
| WO | WO 2007/079153 A2 | 7/2007 |
| WO | WO 2016/003470 A1 | 1/2016 |
| WO | WO 2017/086239 A1 | 5/2017 |

OTHER PUBLICATIONS

Written Opinion for PCT/EP2018/080213, dated Feb. 12, 2019 (PCT/ISA/237).
Office Action in JP Application No. 2020-544117, issued on Aug. 29, 2022.
Office Action in CN Application No. 2018800711052, dated Nov. 3, 2022.
Search Report in CN Application No. 2018800711052, dated Oct. 28, 2022.
British Search Report for GB1718299.9, dated Apr. 5, 2018.
Notice of Reasons for Rejection in corresponding JP application No. 2020-544117, dated May 29, 2023.

* cited by examiner

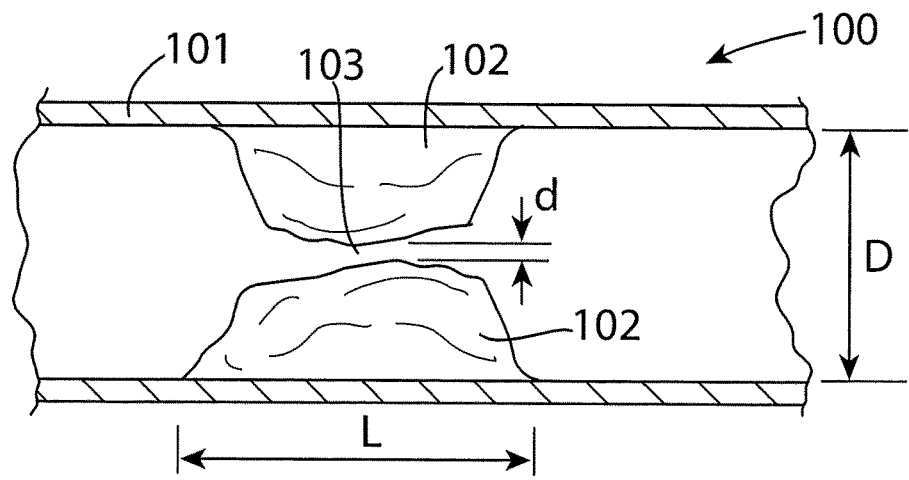
Fig. 1
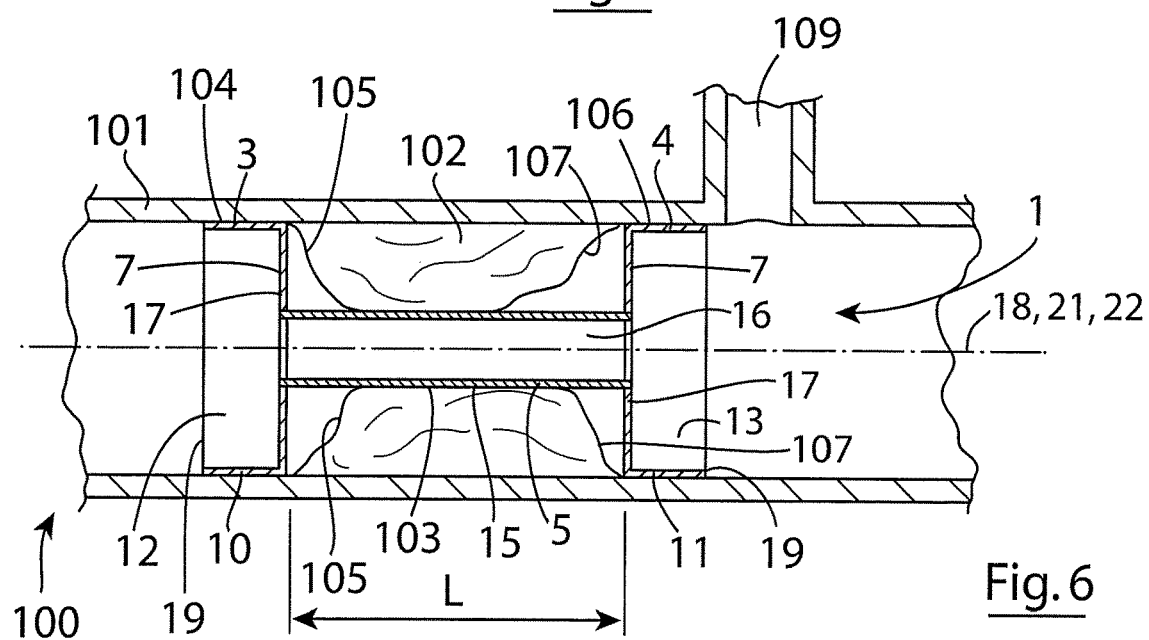
Fig. 6
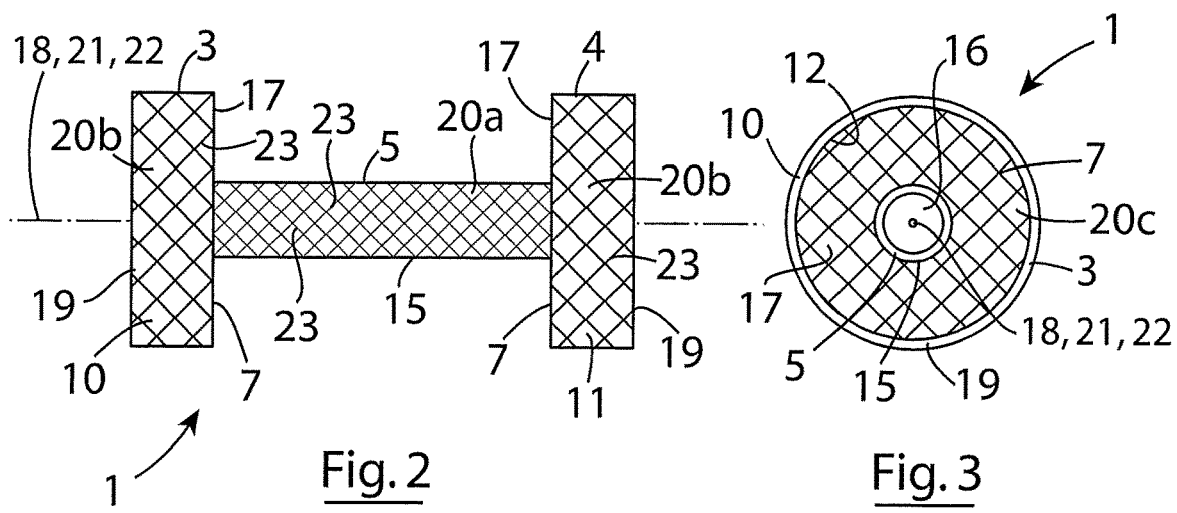
Fig. 2
Fig. 3

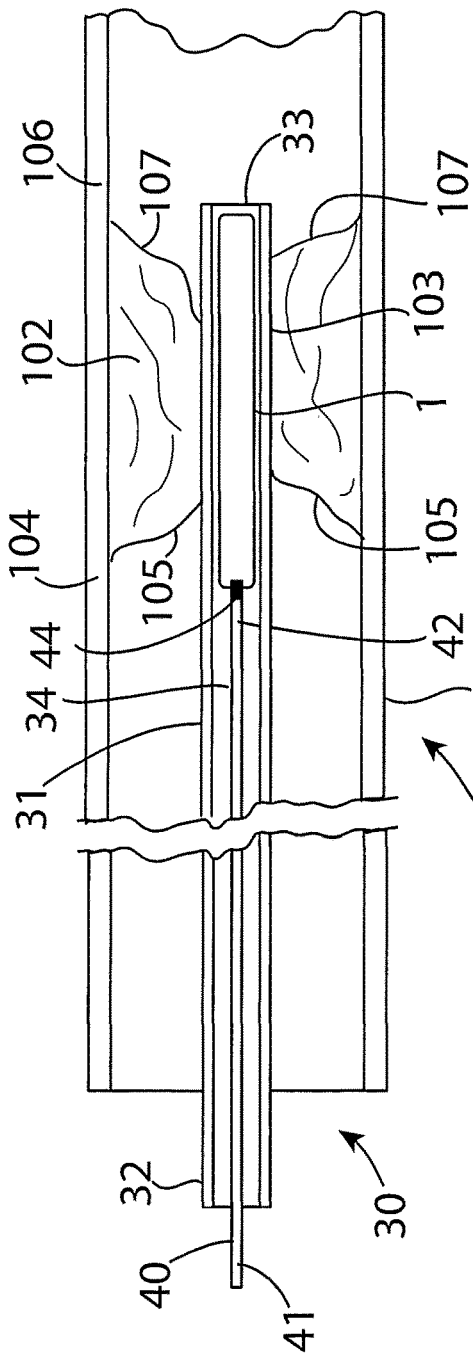
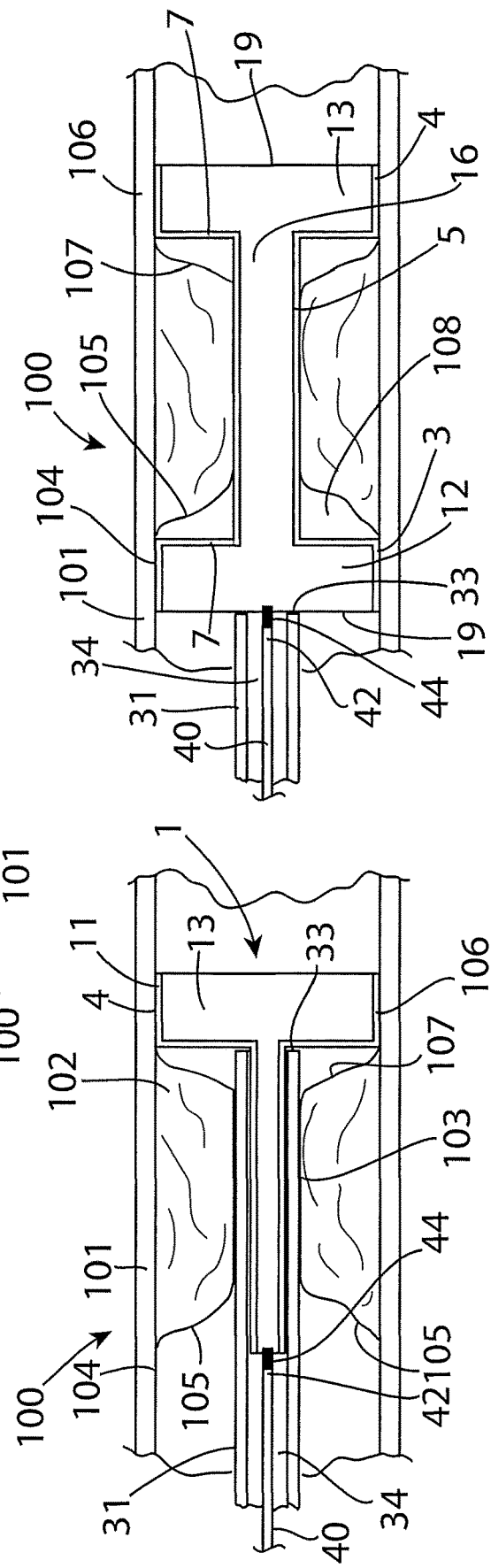
Fig. 7
Fig. 8
Fig. 9

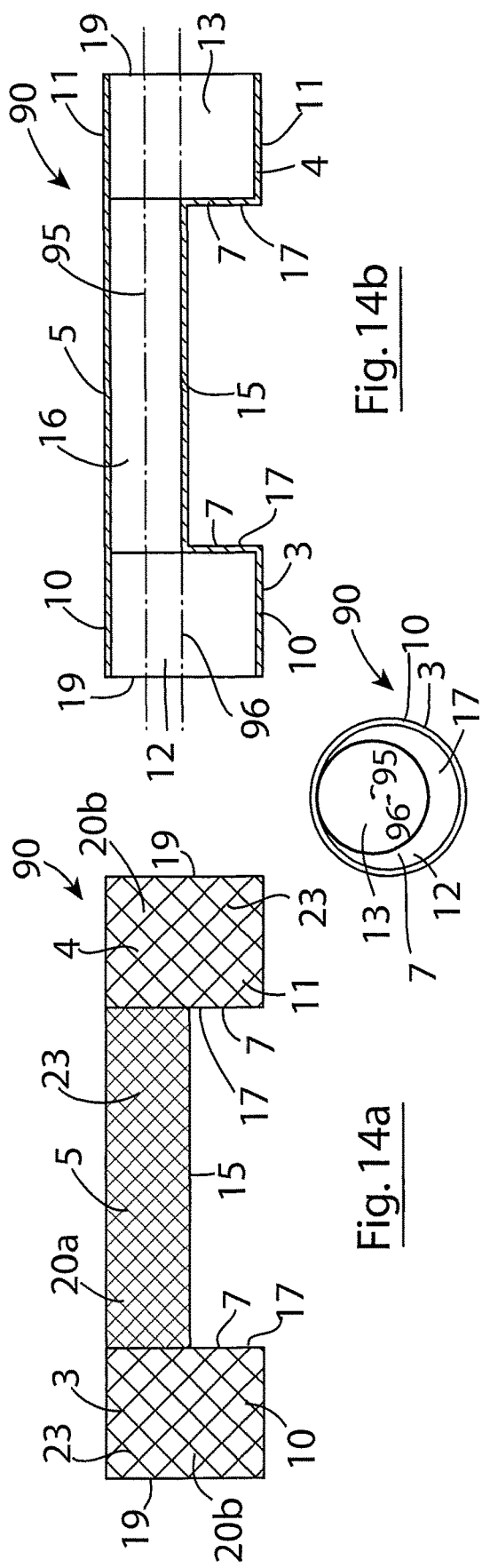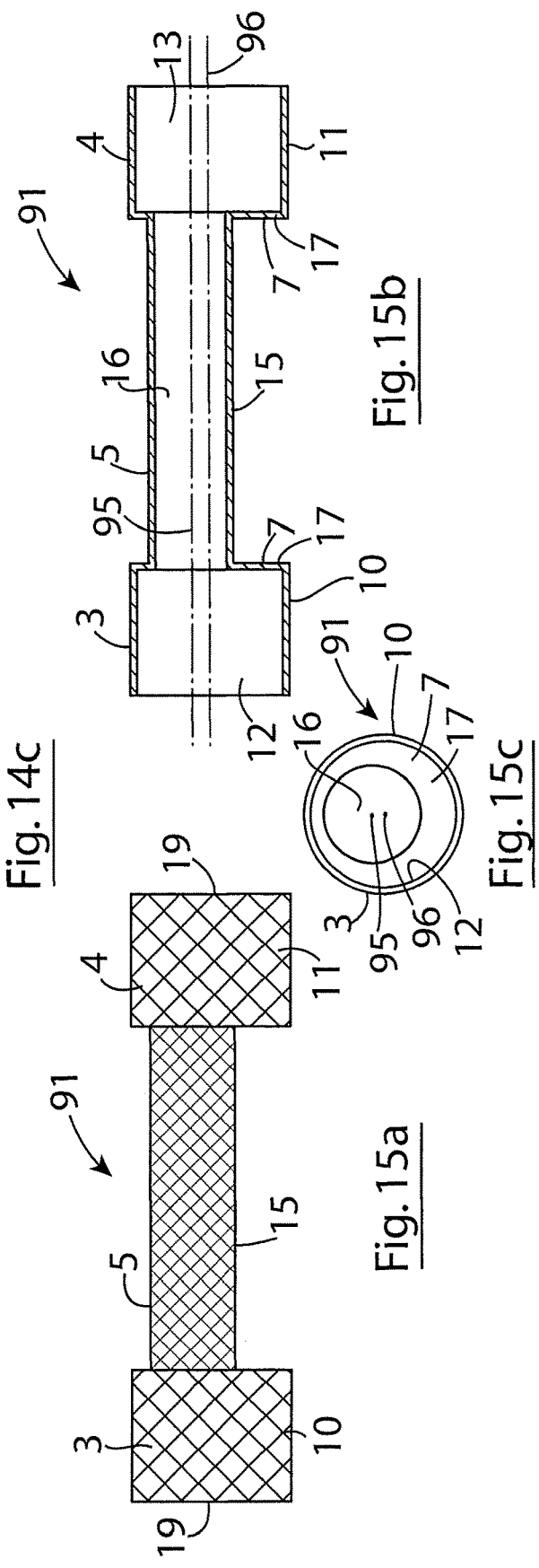

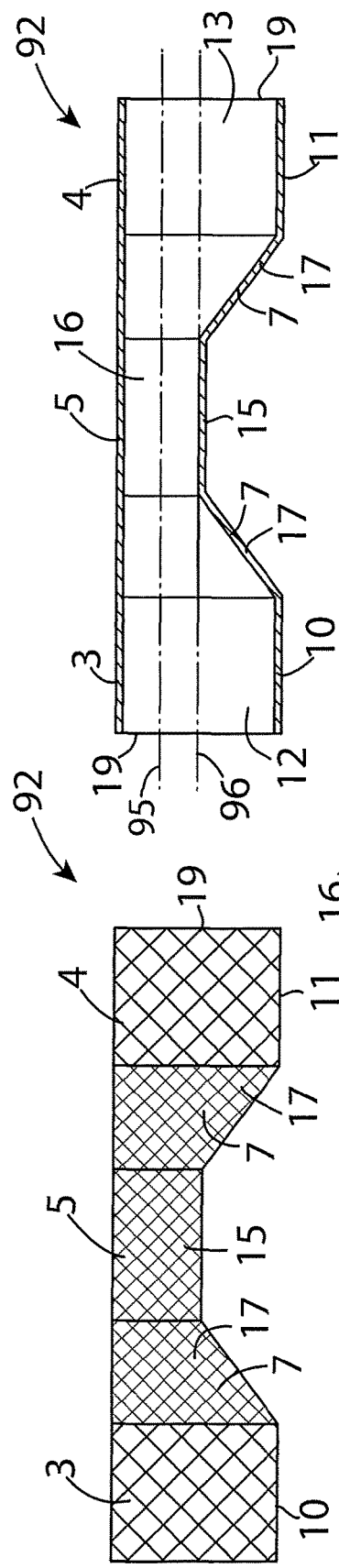
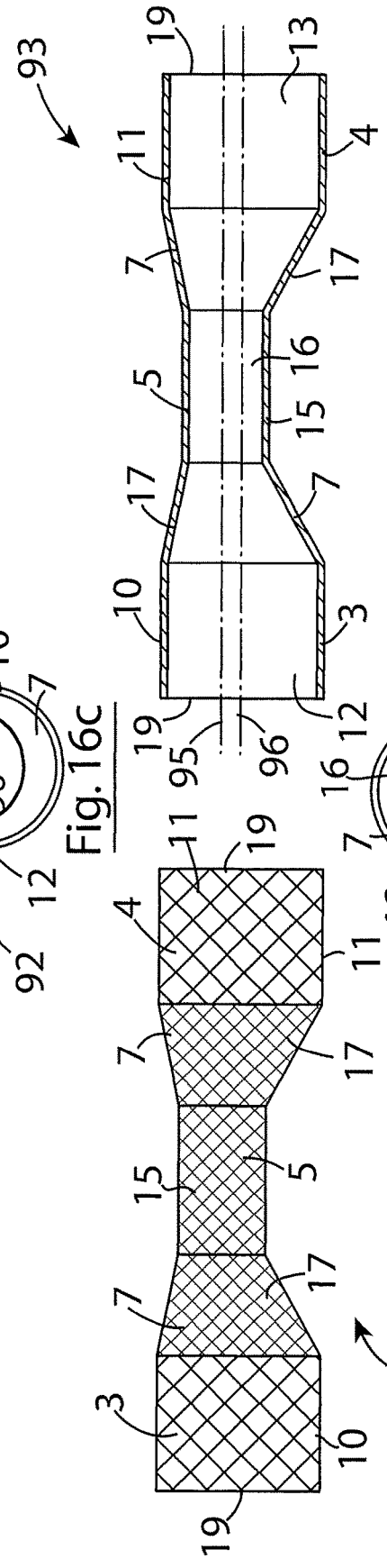
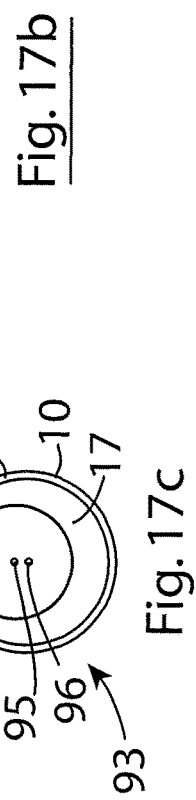
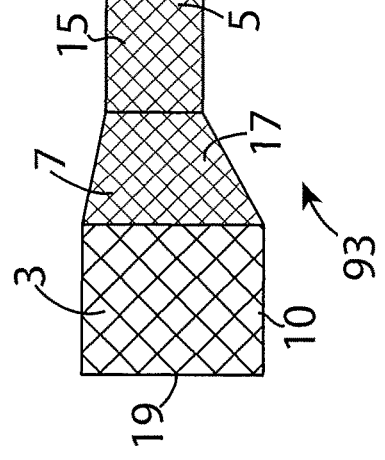

EXPANDABLE STENT AND A METHOD FOR PROMOTING A NATURAL INTRACRANIAL ANGIOGENESIS PROCESS, AND USE OF THE EXPANDABLE STENT IN THE METHOD FOR PROMOTING A NATURAL INTRACRANIAL ANGIOGENESIS PROCESS

CROSS-REFERENCE TO RELATED APPLICATION(S)

This patent application is a continuation of U.S. patent application Ser. No. 17/199,156, filed on Mar. 11, 2021, which is a continuation of U.S. application Ser. No. 16/760,919, issued as U.S. Pat. No. 11,8149,430, filed on May 1, 2020, which is a U.S. national phase entry under 35 U.S.C. § 371 of International Application No. PCT/EP2018/080213, filed on Nov. 5, 2018, which claims the benefit of priority to GB Patent Application No. 1718299.9, filed on Nov. 3, 2017, the entireties of which are incorporated herein by reference.

The present invention relates to an expandable stent, and in particular, though not limited to an expandable stent for use in treating intracranial atherosclerotic disease (ICAD). The stent provides a method to restore sufficient blood flow to mitigate risks of hypoxia, ischemia and infarction, while being mechanically controlled to prevent lesion snow-ploughing. Furthermore the stents of this invention are configured to perfuse downstream tissue to an oligemic state for promoting natural intracranial angiogenesis.

The invention also relates to a method for promoting a natural intracranial angiogenesis process, and further the invention relates to use of the expandable stent in the method for promoting a natural intracranial angiogenesis process. The invention also relates to a method for treating intracranial atherosclerotic disease (ICAD). The invention also relates to use of the expandable stent in the treatment of intracranial atherosclerotic disease.

Intracranial atherosclerotic stenosis (ICAS) is a narrowing (stenosis) of an artery, vein, lumen or other blood vessel, hereinafter referred to as vessels, within the brain caused by a build-up of plaque (atheroma) on the internal arterial wall, thereby reducing blood flow to the brain. This can lead to thromboembolic or haemodynamic ischemic stroke, a leading cause worldwide of disability.

Intracranial atherosclerotic stenosis has a particularly high prevalence amongst certain ethnic groups, the condition being especially prevalent amongst Asians (*Lancet Neurol.* 2013 November; 12(11): 1106-1114). Within Chinese patient populations, the proportion of ischemic stroke which is caused by ICAS can be as high as 50%.

During the early stages of atherosclerosis, fatty material collects along the walls of vessels. The fatty material then thickens, hardens with calcium deposits, which initially results in narrowing of the vessel, and eventually obstruction of the vessel, thereby preventing blood flow through the vessel.

FIG. 1 illustrates an initial narrowing of a diseased intracranial artery 100. The artery 100 comprises a wall 101. A stenosis 102 is formed by plaque on the wall 101. The stenosis 102 of FIG. 1 has not completely blocked the artery 100 but rather has a bore 103 extending therethrough. In FIG. 1 the stenosis 102 is of about 90%; that is to say, about 90% of the healthy diameter of the artery is blocked. This represents a reduction in open cross-sectional area of the artery by a factor of nearly 100. Symptoms can, however, occur at lower levels of stenosis. The plaque may eventually block or fully occlude a vessel or an artery or it may develop a rough surface or thrombus that may repeatedly generate distal emboli. Other plaque characteristics such as intraplaque haemorrhage/haematoma, lipid rich core, thin fibrous cap can also result in plaques which are prone to fracture and lead to clots which block the vessel or repeatedly generate distal emboli.

The current recommended approach for management of ICAS is to use medication, such as blood thinning agents, cholesterol-reducing medications and/or blood-pressure regulating medications. However, the rate of ischemic stroke for ICAS patients treated with medication can be as high as 20% at two years (Chimowitz M I, Lynn M J, Howlett-Smith H, et al. Comparison of warfarin and aspirin for symptomatic intracranial arterial stenosis. N Engl J Med 2005; 31:1305-16) (Nahab F, Cotsonis G, Lynnet M, et al. Prevalence and prognosis of coexistent asymptomatic intracranial stenosis. Stroke 2008; 39:1039-41). In the event that an ICAS patient has been treated with optimal medication, yet has still experienced a second stroke, guidelines allow for further interventions. Currently, the recommended intervention is placement of a stent across the stenosis, performing a balloon angioplasty to open the stenosis, or, more commonly, a combination of both, as a salvage therapy. Stenting acts to widen the stenosis thereby increasing blood flow through the vessel. The stent can also provide a scaffold for a smoother plaque surface to develop and prevent the recurrent generation of distal emboli. However, some studies have indicated that the use of metal stents risks pushing plaques into adjacent, previously-unaffected vessels, by a process called "snow-ploughing". Arterial structures in the brain are highly branched and a recognised problem with existing stents is the snow-ploughing of material from the stenosis into arterial side branches, or so called "perforator" arteries, thereby blocking them and causing strokes in the territories supplied by these side branches. For this reason, the use of stents and/or balloon angioplasty is currently primarily reserved for a follow-up or salvage treatment, once medication has failed.

Accordingly, there is a need to provide an alternative approach for management of ICAS.

The present invention is directed towards providing an expandable stent, and the invention is also directed towards a method for promoting a natural intracranial angiogenesis process, and further, the invention is directed towards use of an expandable stent in a method for promoting a natural intracranial angiogenesis process. The invention is also directed towards an intracranial vessel comprising the expandable stent. The invention is also directed towards a method for treating intracranial atherosclerotic disease, and to use of the expandable stent in the treatment of intracranial atherosclerotic disease. Further, the invention is directed towards the expandable stent for use in treating intracranial atherosclerotic disease, and to the use of the stent in a method to restore sufficient blood flow to mitigate risks of hypoxia, ischemia and infarction, while at the same time being mechanically controlled to prevent lesion snow-ploughing. The invention is also directed towards a stent, a method and use of the stent to perfuse downstream tissue to an oligemic state for promoting natural intracranial angiogenesis.

According to the invention there is provided an expandable stent for stenting a stenosis in an intracranial vessel, the stent in its expanded state being configured to comprise a first end portion having a first bore extending therethrough, a second end portion spaced apart from the first end portion and having a second bore extending therethrough, and a central portion extending between the first and second end portions and having a central bore extending therethrough communicating the first and second bores of the first and second end portions with each other, the central portion being of external transverse cross-section less than the external transverse cross-section of the first and second end portions, wherein the first and second end portions are configured in the expanded state of the stent to engage an arterial wall of the vessel on respective opposite ends of the stenosis to anchor the stent in the vessel, and the central portion is configured in the expanded state of the stent to extend through a bore extending through the stenosis and to bear on the material forming the stenosis with a radial outward pressure to at least prevent further narrowing of the bore through the stenosis.

The invention also provides an intracranial vessel comprising a stenosis, and an expandable stent according to the invention wherein the expandable stent in its expanded state is located in the vessel with the central portion of the stent located in a bore extending through the stenosis and bearing on the material forming the stenosis, and with the first and second end portions of the stent engaging a wall of the vessel on respective opposite ends of the stenosis.

Preferably, the first and second end portions of the stent in the expanded state engage the wall of the vessel adjacent the respective opposite ends of the stenosis Additionally, the invention provides a method for promoting a natural intracranial angiogenesis process to supply blood to an intracranial site being supplied through a vessel having a stenosis therein, the method comprising:

providing an expandable stent, the expandable stent comprising a first end portion having a first bore extending therethrough, a second end portion spaced apart from the first end portion and having a second bore extending therethrough, and a central portion extending between the first and second end portions and having a central bore extending therethrough communicating the first and second bores of the first and second end portions with each other, the central portion being of external transverse cross-section less than the external transverse cross-section of the first and second end portions, placing the expandable stent in an unexpanded state in the stenosis with the central portion of the stent extending through the bore extending through the stenosis and with the first and second end portions on opposite ends of the stenosis, and expanding the stent with the first and second end portions of the expanded stent engaging the wall of the vessel on the respective opposite ends of the stenosis to anchor the stent in the vessel, and with the central portion of the expanded stent bearing on the material forming the stenosis with an outward radial pressure to at least prevent further narrowing of the bore extending through the stenosis in order to promote the natural intracranial angiogenesis process.

Further, the invention provides use of an expandable stent in a method for promoting a natural intracranial angiogenesis process to supply blood to a site being supplied through a vessel having a stenosis therein, the expandable stent comprising a first end portion having a first bore extending therethrough, a second end portion spaced apart from the first end portion and having a second bore extending therethrough, and a central portion extending between the first and second end portions and having a central bore extending therethrough and communicating the first and second end portions with each other, the central portion being of external transverse cross-section less than the external transverse cross-section of the first and second end portions, wherein the expandable stent in an unexpanded state is placed in the stenosis with the central portion of the stent extending through the bore extending through the stenosis and with the first and second end portions on opposite ends of the stenosis, and the stent is expanded to an expanded state with the first and second end portions of the expanded stent engaging the wall of the vessel on respective opposite ends of the stenosis to anchor the stent in the vessel, and with the central portion of the expanded stent bearing on the material forming the stenosis with an outward radial pressure to at least prevent further narrowing of the bore extending through the stenosis in order to promote the natural intracranial angiogenesis process.

In one aspect of the invention the central portion is configured in the expanded state of the stent to bear solely on the material of the stenosis and not on the wall of the vessel.

In another aspect of the invention the first and second end portions are configured in the expanded state of the stent to engage the wall of the vessel adjacent the respective opposite ends of the stenosis.

In another aspect of the invention, the first and second end portions in the expanded state of the stent are of substantially circular transverse cross-section.

In a further aspect of the invention the first and second end portions in the expanded state of the stent are of substantially cylindrical shape.

In another aspect of the invention the first and second end portions are configured in the expanded state of the stent to adapt to the shape of the adjacent part of the vessel.

In another aspect of the invention the central portion in the expanded state of the stent is of substantially circular transverse cross-section.

In a further aspect of the invention the central portion in the expanded state of the stent is of substantially cylindrical shape.

In another aspect of the invention the central portion in the expanded state of the stent is of substantially hourglass shape.

Preferably, the central portion is configured in the expanded state of the stent to adapt to the shape of at least a part of the stenosis.

In one aspect of the invention the central portion is configured to expand to a predefined maximum transverse cross-sectional area in the expanded state of the stent.

Preferably, the predefined maximum transverse cross-sectional area of the central portion is less than the transverse cross-sectional area of a non-diseased part of the vessel adjacent the stenosis, in order to avoid contact of the central portion with the wall of the vessel.

In one aspect of the invention the external diameters of the first and second end portions in the expanded state of the stent do not exceed 5 mm.

Preferably, the external diameters of the first and second end portions in the expanded state of the stent lie in the range of 2 mm to 5 mm.

Advantageously, the external diameters of the first and second end portions in the expanded state of the stent lie in the range of 2.5 mm to 4.5 mm.

In one aspect of the invention the first and second end portions in the expanded state of the stent are configured to expand to a diameter in the range of 100% to 125% of the internal diameter of a non-diseased part of the vessel adjacent the stenosis.

Preferably the first and second end portions in the expanded state of the stent are configured to expand to a diameter in the range of 100% to 110% of the internal diameter of a non-diseased part of the vessel adjacent the stenosis.

In another aspect of the invention the maximum external diameter of the stent in the unexpanded state thereof does not exceed 0.6 mm, and preferably does not exceed 0.5 mm, and advantageously, does not exceed 0.4 mm.

Preferably, the maximum external diameter of the stent in the unexpanded state thereof does not exceed 0.3 mm.

In one aspect of the invention the external diameter of the central portion in the expanded state of the stent lies in the range of 25% to 70% of the external diameters of the first and second end portions.

Preferably, the external diameter of the central portion in the expanded state of the stent lies in the range of 40% to 75% of the external diameters of the first and second end portions.

Advantageously, the external diameter of the central portion in the expanded state of the stent lies in the range of approximately 50% of the external diameters of the first and second end portions.

In one aspect of the invention the external diameters of the first and second end portions in the expanded state of the stent are substantially equal to each other.

In another aspect of the invention the internal diameter of the central portion in the expanded state of the stent lies in the range of 25% to 70% of the internal diameters of the first and second end portions.

Preferably, the internal diameter of the central portion in the expanded state of the stent lies in the range of 40% to 75% of the internal diameters of the first and second end portions.

Advantageously, the internal diameter of the central portion in the expanded state of the stent lies in the range of approximately 50% of the internal diameters of the first and second end portions.

In one aspect of the invention the internal diameters of the first and second end portions in the expanded state of the stent are substantially equal to each other.

In another aspect of the invention the wall thickness of the stent lies in the range of 0.02 mm to 0.15 mm.

Preferably, the wall thickness of the stent lies in the range of 0.05 mm to 0.1 mm.

In one aspect of the invention the central portion in the expanded state of the stent is configured to apply a greater radial outward pressure to the material forming the stenosis than the radial outward pressure applied by the first and second end portions to the wall of the vessel.

In another aspect of the invention the radial outward pressure applied by the central portion in the expanded state of the stent is such as to minimise squashing of the material forming the stenosis to thereby minimise urging the material forming the stenosis longitudinally along the wall of the vessel.

In a further aspect of the invention the first and second end portions in the expanded state of the stent are configured to bear on the wall of the vessel with a pressure sufficient to prevent the material forming the stenosis being urged between the corresponding one of the first and second end portions and the wall of the vessel.

In another aspect of the invention the central portion in the expanded state of the stent is configured to bear on the material forming the stenosis with the radial outward pressure to increase the diameter of the bore extending through the stenosis to a diameter of at least 25% of the non-diseased part of the vessel adjacent the stenosis.

Preferably, the central portion in the expanded state of the stent is configured to bear on the material forming the stenosis with the radial outward pressure to increase the diameter of the bore extending through the stenosis to a diameter of at least 30% of the non-diseased part of the vessel adjacent the stenosis.

Advantageously, the central portion in the expanded state of the stent is configured to bear on the material forming the stenosis with the radial outward pressure to increase the diameter of the bore extending through the stenosis to a diameter of at least 40% of the non-diseased part of the vessel adjacent the stenosis.

Preferably, the central portion in the expanded state of the stent is configured to bear on the material forming the stenosis with the radial outward pressure to increase the diameter of the bore extending through the stenosis to a diameter of at least 50% of the non-diseased part of the vessel adjacent the stenosis, and may increase the diameter of the bore extending through the stenosis to a diameter of at least 70% and even 80% of the non-diseased part of the vessel adjacent the stenosis.

Advantageously, the central portion in the expanded state of the stent is configured to bear on the material forming the stenosis with the radial outward pressure to increase the diameter of the bore extending through the stenosis to a diameter in the order of 60% of the non-diseased part of the vessel adjacent the stenosis.

In one aspect of the invention the central portion terminates at its opposite ends in respective transition portions, and the central portion is connected to and communicates with the first and second end portions through the transition portions.

In another aspect of the invention at least one of the transition portions in the expanded state of the stent extends substantially perpendicularly to the central portion and to the corresponding one of the first and second end portions.

In another aspect of the invention the two transition portions in the expanded state of the stent extend substantially perpendicularly to the central portion and to the corresponding one of the first and second end portions.

In a further aspect of the invention at least one of the transition portions in the expanded state of the stent is of frusto-conical shape.

Preferably, the two transition portions in the expanded state of the stent are of frusto-conical shape.

In one aspect of the invention the frusto-conical portion of each transition portion in the expanded state of the stent defines a cone angle in the range of 30° to 160°.

Preferably, the frusto-conical portion of each transition portion in the expanded state of the stent defines a cone angle in the range of 30° to 110°.

Advantageously, the frusto-conical portion of each transition portion in the expanded state of the stent defines a cone angle in the range of 60° to 110°.

In one aspect of the invention the transition portions in the expanded state of the stent are configured to engage the material forming the stenosis adjacent the respective opposite ends thereof.

Preferably, the first and second end portions and the central portion are of one of cage like construction, braided construction and perforated construction defining interstices therein.

In another aspect of the invention the interstices in the central portion in the expanded state of the stent are of smaller area than the interstices in the first and second end portions.

Preferably, the interstices in the central portion in the expanded state of the stent are of sufficiently small area to one of minimise and prevent the material forming the stenosis passing therethrough. Advantageously, the interstices in the transition portions in the expanded state of the stent are of smaller area than the area of the interstices in the first and second end portions.

In another aspect of the invention the interstices in the transition portions in the expanded state of the stent are of sufficiently small area to one of minimise and prevent the material forming the stenosis passing therethrough.

In one embodiment of the invention the central portion of the stent defines a longitudinally extending main central axis, the first end portion defines a longitudinally extending first central axis, and the second end portion defines a longitudinally extending second central axis.

In another embodiment of the invention the main central axis, the first central axis and the second central axis coincide with each other.

In another aspect of the invention the main central axis is offset from the first and second central axes.

In a further aspect of the invention the first and second central axes coincide with each other.

In another aspect of the invention the main central axis extends parallel to the first and second central axes.

In a further aspect of the invention the main central axis extends at an angle greater than 0° to the first and second central axes.

In one aspect of the invention the stent is configured to expand at blood temperature of a human or animal subject.

In another aspect of the invention a biocompatible film is provided on the surface of the stent.

In a further aspect of the invention the biocompatible film is implanted with a medication to prevent further growth of atherosclerotic plaque.

In another aspect of the invention the stent is implanted at a molecular level or coated with one of a medication to reduce the thrombotic potential of the stent and a material to promote angiogenesis.

In one aspect of the invention the stent is coated with a therapeutically active material. Preferably, the therapeutically active material comprises an angiogenesis promoting material.

Advantageously, the angiogenesis promoting material composes methacrylic acid-co-isodecyl acrylate (MAA-co-IDA; 40% MAA).

In another aspect of the invention the stent is configured to minimise endothelial shear stress resulting from the stent.

Preferably, the stent is configured so that the endothelial shear stress resulting from the stent does not exceed 250 Pa.

In one aspect of the invention the stent comprises a biocompatible material.

In another aspect of the invention the stent comprises a biocompatible biodegradable material.

In a further aspect of the invention the stent comprises a polymer material.

In another aspect of the invention the stent comprises a self-expanding material.

In a further aspect of the invention the stent comprises a memory material.

In another aspect of the invention the stent comprises an alloy selected from one or more of the following metals:
Nickel, titanium, cobalt, stainless steel.

In a further aspect of the invention the stent comprises a non-self-expanding material.

In one aspect of the invention the first and second end portions in the expanded state of the stent engage the wall of the vessel adjacent the respective opposite ends of the stenosis.

In another aspect of the invention the first and second end portions in the expanded state of the stent are of substantially circular transverse cross-section.

In a further aspect of the invention the first and second end portions in the expanded state of the stent are of substantially cylindrical shape.

In another aspect of the invention the first and second end portions in the expanded state of the stent adapt to the shape of the adjacent part of the vessel.

In one aspect of the invention the stent is expanded to the extent that the central portion increases the diameter of the bore extending through the stenosis to an extent to increase the rate of the blood flow flowing through the stenosis to lie in the range of 25% to 80% of the normal blood flow rate through the vessel without the stenosis.

In another aspect of the invention the stent is expanded to the extent that the central portion increases the diameter of the bore extending through the stenosis to an extent to increase the rate of the blood flow flowing through the stenosis to lie in the range of 30% to 70% of the normal blood flow rate through the vessel without the stenosis.

In a further aspect of the invention the stent is expanded to the extent that the central portion increases the diameter of the bore extending through the stenosis to an extent to increase the rate of the blood flow flowing through the stenosis to lie in the range of 40% to 60% of the normal blood flow rate through the vessel without the stenosis.

Preferably, the stent is expanded to the extent that the central portion increases the diameter of the bore extending through the stenosis to an extent to increase the rate of the blood flow flowing through the stenosis to lie in the range of approximately 50% of the normal blood flow rate through the vessel without the stenosis.

Further the invention provides a method of treating intracranial atherosclerosis disease in a subject, the method comprising the steps of scaffolding the lesion to control migration of atherosclerotic material, dilating the bore of the lesion such that downstream tissue is maintained in an oligemic state, and preferably, the method comprises medicating the patient to promote the development of collateral vessels to support said oligemic tissue.

Further the invention provides a method for treating a patient that has an intracranial stenosis, the method comprising the steps of measuring the length of the stenosis, measuring the diameter of a bore extending through the stenosis, and measuring the diameters of the vessel adjacent the distal and proximal ends of the stenosis, selecting a stent with a central portion having a diameter that is at least 50% of the diameter of the vessel adjacent one of the proximal and distal ends of the stenosis, and placing the stent in the vessel with the central portion of the stent extending through the bore of the stenosis, and configuring the stent to remodel the stenosis to increase the diameter of the bore extending through the stenosis to a diameter preferably of at least 50% of the diameter of the vessel adjacent the proximal end of the stenosis. Preferably, the stent is configured to remodel the stenosis within thirty days of placing the stent in the vessel.

The invention also provides a method for preventing a secondary infarction when treating a stenosis in a vessel of a subject with a branch vessel adjacent the stenosis, the method comprising providing a stent that is configured to under perfuse downstream tissue, positioning the stent relative to the stenosis, and expanding the stent to an hourglass shape to conform to the stenosis, and confirming the preservation of said branch vessel before implanting the stent.

Further, the invention provides a method for treating a human or animal subject to restore sufficient blood flow through a vessel in an intracranial vascular system to mitigate the risk of one or more of hypoxia, ischemia and infarction, the method comprising provided the expandable stent according to the invention, loading the expandable stent in a collapsed state into a proximal end of a lumen extending through a delivery microcatheter, the distal end of the delivery microcatheter being positioned across the stenosis, advancing the stent in the collapsed state through the lumen of the delivery microcatheter and positioning the stent in its collapsed state within the lumen of the delivery microcatheter adjacent the distal end thereof, such that the central portion of the stent in its collapsed is located within the bore of the stenosis. Preferably, the method further comprises withdrawing the delivery microcatheter while holding the stent with the central portion thereof located within the bore of the stenosis to expose the second end portion of the stent. Preferably, the axial position of the delivery microcatheter is adjusted along with the axial position of the stent so that one of the first end portion and the second end portion of the stent is located in the vessel adjacent a distal end of the stenosis.

Preferably, the method further comprises further withdrawing the delivery microcatheter to expose the entire stent.

Preferably, the method further comprises expanding the stent to scaffold the stenosis.

In one aspect of the invention, the method comprises confirming the position of the stent by fluoroscopy.

Preferably, the method comprises decoupling the stent from the delivery microcatheter or other element of a delivery system.

In another embodiment of the invention, the method comprises capturing an angiographic image of the stent in the stenosis to confirm the position of the stent.

In another aspect of the invention the method further comprises removing the delivery catheter from the subject.

In another aspect of the invention the method comprises providing the expandable stent with a central portion of hourglass shape.

In a further aspect of the invention the expandable stent comprises a radiopaque marker, and preferably, the radiopaque marker is located on one or both of the first end portion and the second end portion of the stent.

In another aspect of the invention the radiopaque markers are located adjacent the portion of the central portion of hourglass shape of minimum diameter.

In another aspect of the invention the method comprises visualising the stenosis using fluoroscopy and dimensioning key features of the stenosis prior to treatment.

Preferably, the method comprises computing dimensions of the most suitable shape of the central portion of the stent of hourglass shape for the stenosis.

In another aspect of the invention the method comprises positioning the stent in the collapsed state under fluoroscopic guidance, such that the central portion of the stent of hourglass shape is located in the stenosis.

Preferably, the stent is expanded with the central portion of hourglass shape located in the stenosis for dilating the bore extending through the stenosis to perfuse distal tissue to an oligemic state.

Preferably, the transition portions are configured into an undulating tubular body.

Advantageously, the first and second end portions, the transition portions and the central portion are configured into a monolith structure.

In one embodiment of the invention the transverse cross-sectional area of the bore through the stenosis is increased by 3080% while the vessel adjacent the stenosis is dilated by less than 18%.

In another embodiment of the invention the transverse cross-sectional area of the bore through the stenosis is increased by 2000% while the vessel adjacent the stenosis is dilated by less than 14%.

In another embodiment of the invention the transverse cross-sectional area of the bore through the stenosis is increased by 1000% while the vessel adjacent the stenosis is dilated by less than 16%.

In another embodiment of the invention the transverse cross-sectional area of the bore through the stenosis is increased by 3000% while the vessel adjacent the stenosis is dilated by less than 12%.

Preferably, the transverse cross-sectional area of the bore through the stenosis is increased in the range of 1000% to 3000% while the vessel adjacent the stenosis is dilated in the range of 10% to 18%.

The advantages of the invention are many. Essentially, the expandable stent according to the invention when located in a stenosis in a vessel within the intracranial vascular branched system is not intended to fully reinstate a partially occluded vessel to its fully normal state nor to its original internal diameter, but rather, to maintain blood flow through the vessel at a partially restricted level, or to increase the rate of the blood flow through the vessel to a flow rate anywhere in the range of 25% to 80% of the normal flow rate through that vessel prior to the formation of the stenosis, and preferably, to increase the rate of blood flow to approximately 50% of the normal flow rate through the vessel prior to the formation of the stenosis. This allows sufficient time to allow natural intracranial angiogenesis within the intracranial vascular system proceed, whereby collateral blood vessels grow in order to allow the site or sites being supplied with blood through the diseased vessel to be supplied through one or more alternative vessels which may or may not already supply the site which is supplied by the diseased vessel. Thus, on completion of the natural intracranial angiogenesis process the site being supplied by the diseased vessel is fully supplied with a blood supply from the newly grown collateral vessels resulting from the natural intracranial angiogenesis process.

The stents according to the invention are also configured to treat brain artery lesions that carry significant risk for patients. These lesions have a high level of restriction (stenosis) and the shear forces of high velocity blood flowing through these lesions puts the patient at high risk of a stroke. At the same time intracranial vessels in human subjects are thinner than in other parts of the body and are thus more fragile than vessels of similar size in the heart or the kidneys or elsewhere. Aggressive stenting in these vessels has been shown to be inferior to medical therapy. In one embodiment this invention provides an entirely new strategy for treating these patients. The method of partially dilating these intracranial stenoses with the devices of this invention has the effect of restoring sufficient blood flow to ensure that the downstream tissue is not hypoxic while at the same time preserving an oligemic state in the vascular bed. This oligemic state in the intracranial vascular bed promotes the development of collateral vessels (new vessels) in the brain in an angiogenesis process and this therapeutic strategy allows the brain to evolve its own circulatory redundancy over time. This has the effect of reducing the risk that the stenosis presents to the patient. Even an acute occlusion at the site of the original lesion may not significantly harm the patient in situation where collateral vessels have developed.

Another aspect of the expandable stent of this invention is the way in which it manages the atherosclerotic material that makes up the body of the restriction (stenosis). In a conventional stenting procedure this material is aggressively displaced and it causes the native artery to expand to accommodate. The expandable stents of this invention avoid this aggressive action and displace atherosclerotic material to very minimal levels.

Accordingly, the expandable stent according to the invention, while in general it is used to increase blood flow through the diseased vessel, it is not used to reinstate normal blood flow through the diseased vessel, since to increase the diameter of the bore extending through the stenosis to reinstate normal blood flow through the diseased vessel would, in general, result in the material forming the stenosis being squashed and spread longitudinally along the vessel wall. Due to the large number of branched vessels in the intracranial vascular system and the closeness of the branches extending from a main vessel or artery this would result in the material forming the stenosis being spread past one or more branched vessels adjacent the stenosis thereby blocking the branched vessels. The squashing and spreading of material forming the stenosis beyond a stent, generally is referred to as "snow-ploughing". The expandable stent according to the invention and its use avoids the danger of snow-ploughing, and thus blocking branched vessels or arteries adjacent to the stenosis, while at the same time maintaining a flow of blood through the diseased vessel or artery sufficient to promote and support the natural intracranial angiogenesis process until it has been completed, and new or collateral blood vessels have grown in order to provide an alternative blood supply to the site or sites supplied by the diseased vessel.

A further advantage of the invention is that by only partly opening the bore through the stenosis, the risk of intracranial hyperperfusion injury is reduced, and in general avoided. Intracranial hyperperfusion injury can result from rapid restoration of normal perfusion pressure, and may potentially lead to intracranial haemorrhage. Intracranial hyperperfusion may also involve dysregulation of the intracranial vascular system and hypertension, in the setting of an increase in the intracranial blood flow.

Accordingly, the advantages of the invention are many. Firstly, the expandable stent avoids snow-ploughing of material forming a stenosis which would otherwise block an adjacent branched vessel or branched vessels adjacent the stenosis. In the neurovascular circulation some of these branched vessels are called perforators because they originate from vessels that sit in the folds of the brain (ex middle intracranial artery) and they perforate into intracranial tissue of the brain. It is the case that some of these perforator vessels are associated with very high level functions such as speech and so an occlusion of one of these tiny vessels can have devastating consequences for the patient. The expandable stent of this invention is configured to protect these perforator vessels from being occluded by snow-ploughing while restoring blood flow to an oligemic level. The expandable stent while avoiding snow-ploughing of the material forming the stenosis at the same time maintains, or increases the diameter of the bore extending through the stenosis to an extent that blood flow through the diseased vessel is maintained at a value of greater than 30% of normal and preferably approximately 50% of normal, thereby permitting natural intracranial angiogenesis processes to proceed. The expandable stent according to the invention maintains the flow of blood at a sufficient flow rate at least until the natural intracranial angiogenesis processes have been completed and new or collateral blood vessels have been grown in order to supply the sites which had originally been supplied by the diseased vessel or artery. Due to the fact that the blood flow is maintained at a value of 50% of the normal blood flow rate intracranial hyperperfusion is avoided, and the risk of stroke is also low. Although in some cases the expandable stent may be configured to increase the flow rate of blood to 70% of normal, and in some limited cases to 80% of normal.

Figure 4:
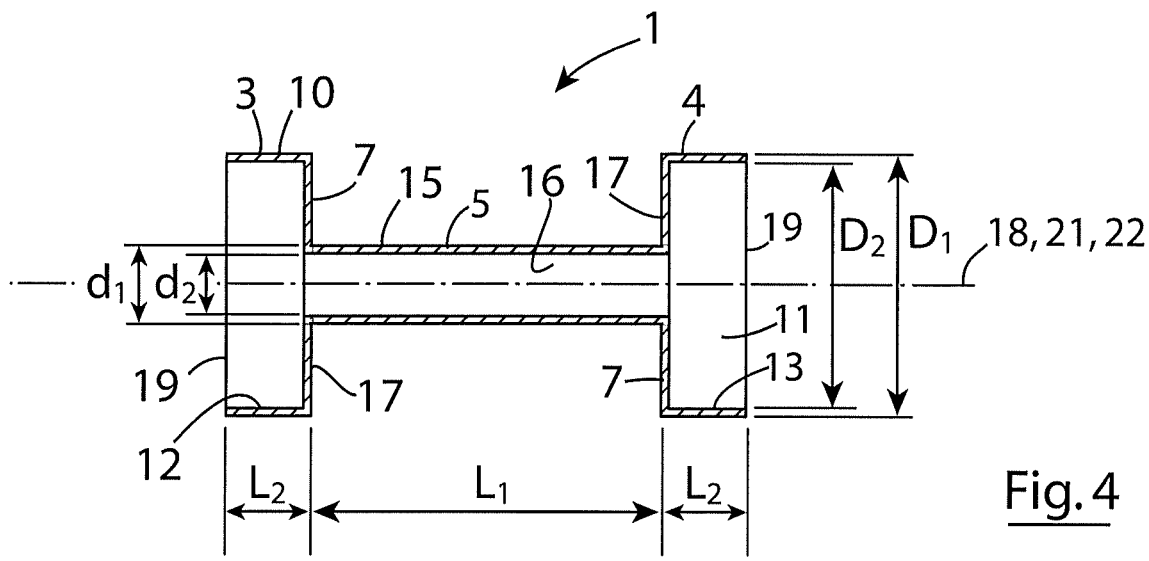
Figure 10:
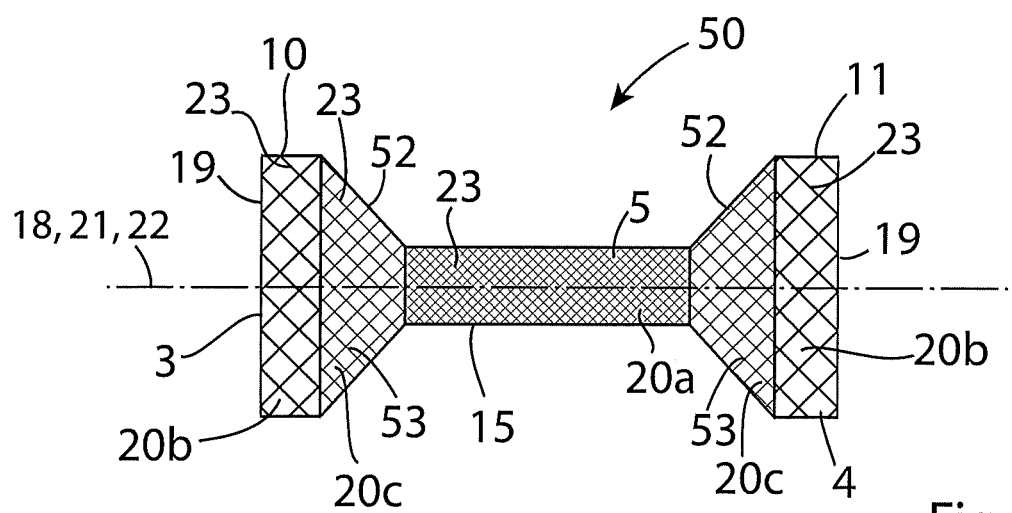
Figure 11:
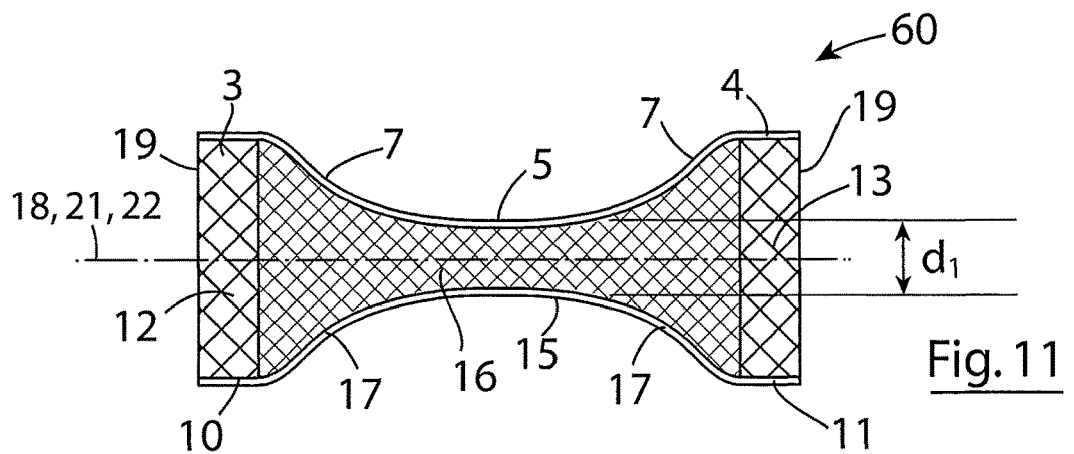
Figure 12:
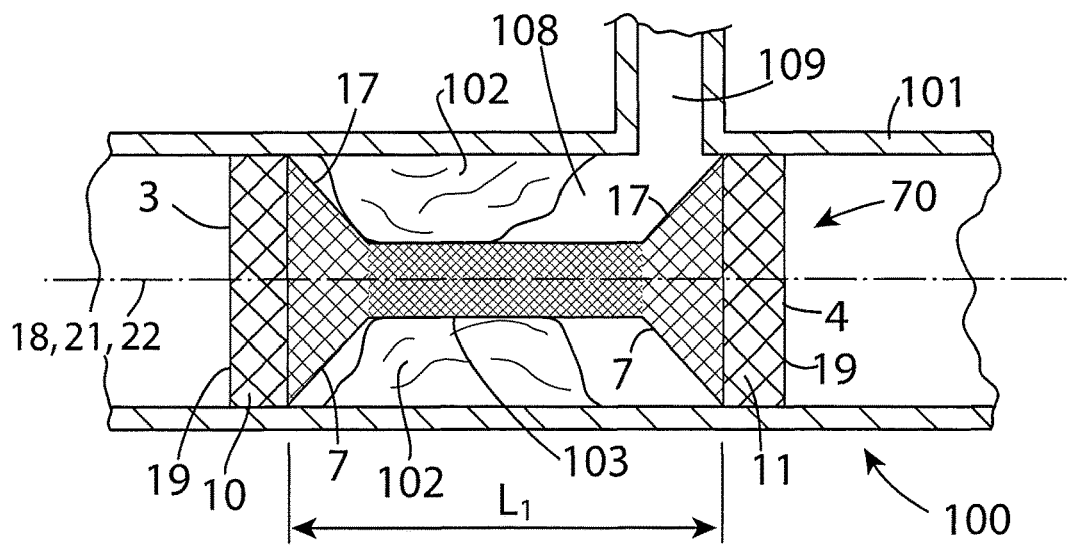
Figure 13:
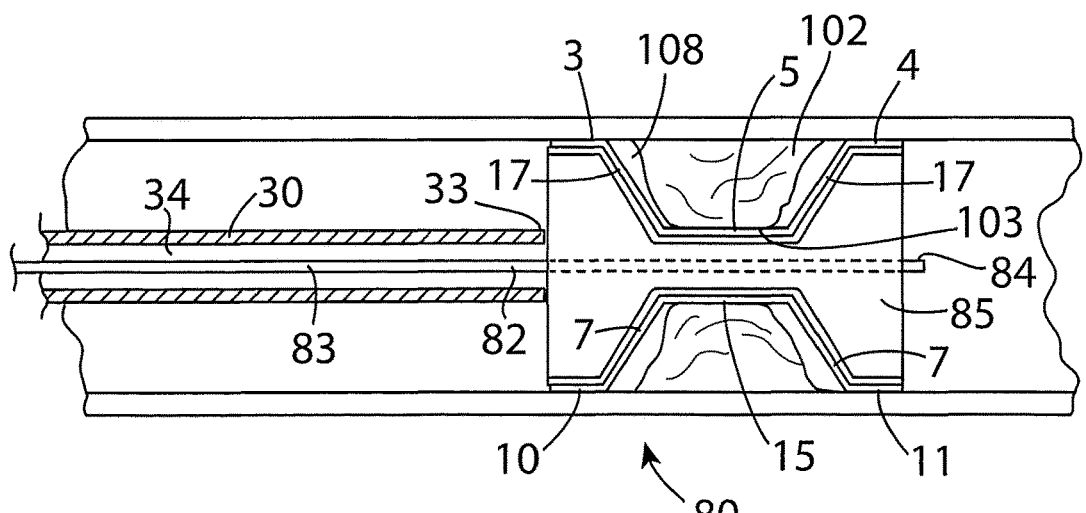
Figure 18:
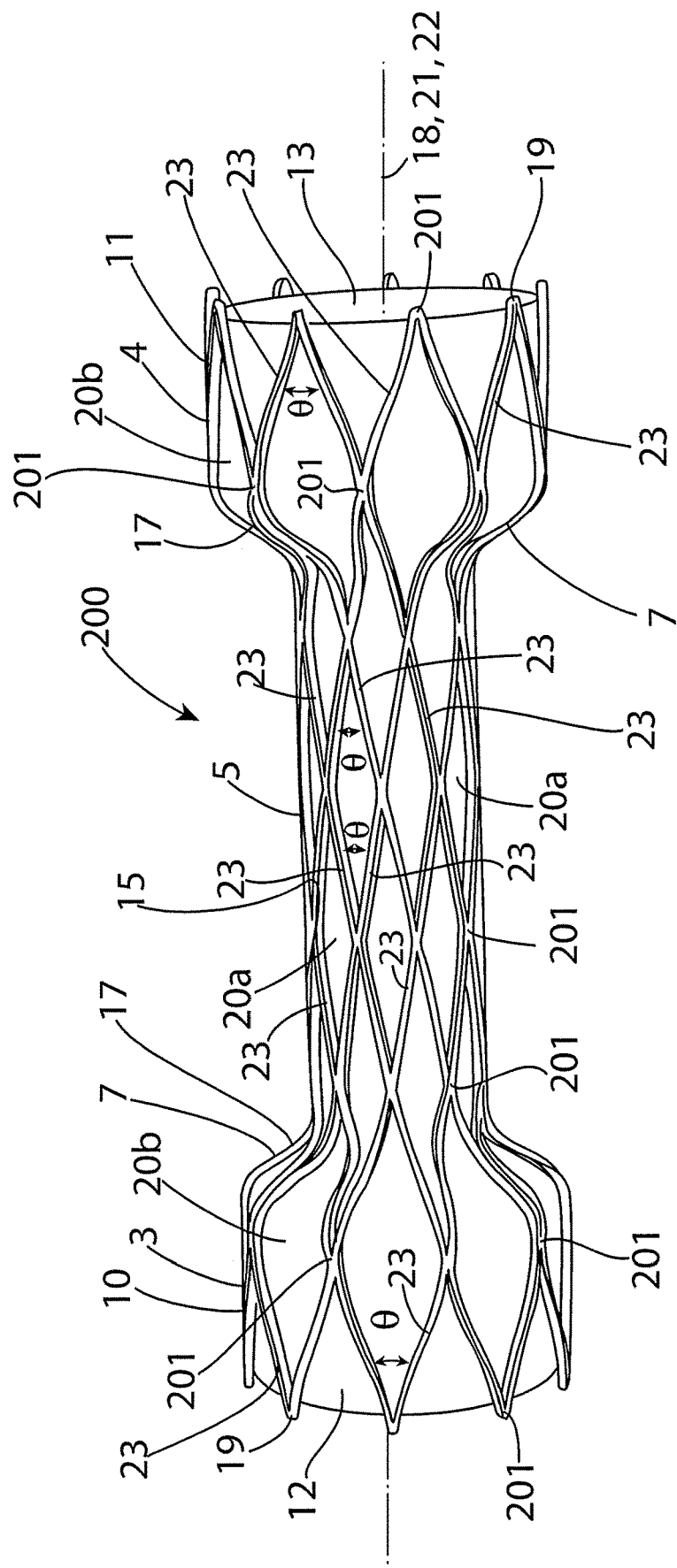

The invention and its many advantages will be more clearly understood from the following description of some preferred embodiments thereof which are given by way of example only with reference to the accompanying drawings, in which:

FIG. 1 is a cross-sectional side elevational view of a disease intracranial artery, FIG. 2 is a side elevational view of an expandable stent according to the invention for use in maintaining blood flow through a stenosis in the diseased artery of FIG. 1, FIG. 3 is an end elevational view of the stent of FIG. 2, FIG. 4 is a cross-sectional side elevational view of the stent of FIG. 2, FIG. 5 is a cross-sectional side elevational view of the stent of FIG. 2 in an unexpanded state, FIG. 6 is a cross-sectional side elevational view of the stent of FIG. 2 in use in the artery of FIG. 1, FIG. 7 is a cross-sectional side elevational view of a delivery system for delivering the stent of FIG. 2 into the stenosis of the diseased artery, FIG. 8 is a cross-sectional side elevational view of a portion of the artery of FIG. 7 illustrating the stent of FIG. 2 being positioned in the stenosis of the diseased artery, FIG. 9 is a view similar to FIG. 8 further illustrating the placing of the stent of FIG. 2 in the diseased artery, FIG. 10 is a side elevational view of an expandable stent according to another embodiment of the invention, FIG. 11 is a cross-sectional side elevational view of a stent according to another embodiment of the invention, FIG. 12 is a cross-sectional side elevational view of a stent according to a further embodiment of the invention illustrated in a stenosis in a diseased artery, FIG. 13 is a cross-sectional side elevational view of a stent according to a further embodiment of the invention illustrated being placed in a stenosis in an artery, FIGS. 14a, b and c are side elevational, cross-sectional side elevational and end elevational views of a stent according to another embodiment of the invention, FIGS. 15a, b and c are side elevational, cross-sectional side elevational and end elevational views of a stent according to another embodiment of the invention, FIGS. 16a, b and c are side elevational, cross-sectional side elevational and end elevational views of a stent according to another embodiment of the invention, FIGS. 17a, b and c are side elevational, cross-sectional side elevational and end elevational views of a stent according to another embodiment of the invention, and FIG. 18 is a perspective view of a stent according to another embodiment of the invention.

Referring to the drawings and initially to FIGS. 2 to 6 thereof, there is illustrated an expandable stent according to the invention indicated generally by the reference numeral 1. The stent 1 is expandable from an unexpanded state illustrated in FIG. 5 to an expanded state illustrated in FIGS.

2,3,4 and 6. The stent 1 is of dimensions in the unexpanded state which are suitable for urging the stent through the intracranial vascular system (not shown) in a delivery microcatheter, as will be discussed below, to a stenosis, for example, the stenosis 102 in an intracranial artery, for example, the diseased intracranial artery 100 of the intracranial vascular system (not shown). In the expanded state the dimensions of the stent 1 are such that the stent 1 expands in the stenosis 102 in order to maintain the bore 103 through the stenosis 102 open and/or to increase the transverse cross-sectional area of the bore 103 through the stenosis 102 in order to maintain and/or increase the rate of blood flow through the stenosis 102. Maintaining or increasing the rate of blood flow through the stenosis 102 protects downstream tissue, namely, tissue supplied with blood through the artery 100, from hypoxia, ischemia and/or infarction while maintaining the downstream tissue in an oligemic state. This thus promotes a natural intracranial angiogenesis process and allows the natural intracranial angiogenesis process to be completed, whereby new collateral blood vessels are grown to supply the downstream tissue which is being supplied through the diseased artery 100. The dimensions of the stent 1 in the expanded state and the unexpanded state are discussed in more detail below.

The stent 1 in its expanded state comprises a first end portion 3 and a second end portion 4, both of circular transverse cross-section and of the same external and internal diameters. A central portion 5 also of circular transverse cross-section extends between the first and second end portions 3 and 4 and terminates at its opposite ends in respective transition portions 7 which connect the central portion 5 to the corresponding ones of the first and second end portions 3 and 4. In this embodiment of the invention when the stent 1 is in its expanded state the transition portions 7 extend substantially perpendicularly from the central portion 5, and perpendicularly from the corresponding one of the first and second portions 3 and 4. However, as discussed below with reference to FIGS. 11 to 13, the transition portions 7 may be, for example, frusto-conical of progressively increasing transverse cross-sectional area from the central portion 5 to the first and second end portions 3 and 4, and indeed in other embodiments of the invention, such stents as the stents described with reference to FIGS. 11 to 13 may be preferable to the stent 1.

The first and second end portions 3 and 4 are formed by expandable first and second walls 10 and 11, respectively, having first and second bores 12 and 13 extending therethrough. The central portion 5 comprises an expandable central wall 15 having a bore 16 extending therethrough communicating the first and second bores 12 and 13 of the first and second end portions 3 and 4, respectively. In this embodiment of the invention in the expanded state of the stent 1, the first, second, and central walls 10, 11 and 15, respectively, are cylindrical. In this embodiment of the invention the transition portions 7 are formed by respective transition walls 17, which are expandable, and in the expanded state of the stent 1 expand outwardly so that the transition walls 17 extend perpendicularly from the central wall 15 and from the first and second walls 10 and 11. The central wall 15 of the central portion 5 defines a longitudinally extending main central axis 18, and the first and second walls 10 and 11 of the first and second end portions 3 and 4 defined respective longitudinally extending first and second central axes 21 and 22, respectively. In this embodiment of the invention the first and second end portions 3 and 4 are axially aligned with each other, and the central portion 5 is axially aligned with the first and second end portions 3 and 4. Accordingly, in this embodiment of the invention the first and second central axes 21 and 22 and the main central axis 18 coincide with each other.

It is envisaged, and indeed will be appreciated by those skilled in the art that the first and second walls 10 and 11 and the central wall 15 need not necessarily be cylindrical. For example, it is envisaged that in the expanded state of the stent 1, the central wall 15 may diverge outwardly from a central point intermediate the transition walls 17 towards the transition walls 17, in other words, the central wall 15 may be of "hourglass" shape, whereby the diameter of the central wall 15 adjacent the transition walls 17 would be greater than the diameter of the central wall 15 at the central point midway between the transition walls 17, in which case, the diameter of the diverging portions of the cylindrical wall 15 would increase gradually from the central point of the central wall 15 towards the transition walls 17. Indeed, it is envisaged that when the stent 1 is expanded in situ, depending on the shape of the bore 103 extending through the stenosis 102, the central wall 15 may take up a shape corresponding to the profile of the bore 103 extending through the stenosis 102.

It is also envisaged that the first and second walls 10 and 11 of the first and second end portions 3 and 4 may be of shape other than cylindrical, and in some embodiments of the invention, it is envisaged that the first and second walls 10 and 11 in the expanded state of the stent 1 may take up a shape whereby the first and second walls 10 and 11 converge in a longitudinal direction from the transition wall 17, or may converge from a central point midway between the corresponding transition wall 17 and a corresponding free end 19 of the end walls 10 and 11 towards the corresponding transition wall 17 and the corresponding free end 19. Indeed, when in situ, it is envisaged that the first and second walls 10 and 11 of the first and second end portions 3 and 4 may take up a shape which would correspond to the longitudinal profile of respective proximal and distal non-diseased portions 104 and 106, respectively, of the artery adjacent a proximal end 105 and a distal end 107, respectively, of the stenosis 102.

Needless to say, the central wall 15 of the central portion 5 and the first and second walls 10 and 11 of the first and second end portions 3 and 4 may take up any suitable shape in the expanded state of the stent 1 and also when the stent 1 is located in situ in the artery 100, for example, the external surfaces of the first and second end walls 10 and 11 and the central wall 15 may be concave or convex.

It will also be appreciated that in some embodiments of the invention the first and second end portions may not be axially aligned with each other, and furthermore, the central portion 15 may not be axially aligned with the first and second end portions 2 and 3. In which case, only the central axes 18, 21 and 22 of those portions of the central portion 18 and the first and second end portions 3 and 4 which are axially aligned with each other will coincide. For example, in cases where the first and second end portions 3 and 4 are axially aligned, the first and second central axes 21 and 22 will coincide with each other, and in cases where the central portion 5 is not axially aligned with the first and second end portions 3 and 4, the main central axis 18 of the central portion 15 will be offset from the first and second central axes 21 and 22 of the first and second end portions 3 and 4. In general, in such a case, the main central axis 18 would extend parallel to the first and second central axes 21 and 22 of the first and second end portions 3 and 4. Although, it is envisaged that in some cases the main central axis 18 of the central portion 5 may extend at an angle to the first and second central axes 21 and 22 of the first and second end portions 3 and 4. Indeed, in use, depending on the shape and angle of the bore 103 extending through the stenosis 102, the central portion 5 may take up an orientation which would extend at an angle to the first and second end portions 3 and 4. In which case, it is envisaged that the first and second central axes of the first and second end portions 3 and 4 may not be axially aligned, but would be offset from each other, and the main central axis 18 of the central portion 5 would extend at an angle to the first and second central axes 21 and 22 of the first and second end portions 3 and 4. Additionally, in the event of the stenosis 102 being located in a curved or angled artery, the first and second central axes 21 and 22 of the first and second end portions 3 and 4 may extend at an angle to each other, and also at respective different angles to the main central axis 18 of the central portion 5.

The dimensions of the stent 1 in the expanded state in general, are chosen based on the diameter of the stenosis 102, and the length of the stenosis 102, and also on the diameter of the non-diseased portion of the artery 100 adjacent the stenosis 102. In general, the stents 1 will be provided with the first and second end portions 3 and 4 and the central portion 5, as well as the transition portions 7 in a range of different diameters and lengths in order to accommodate arteries or vessels of different diameters and stenoses of different lengths, and having bores extending therethrough of different diameters. The selection of a stent for a particular stenosis in a particular artery or vessel in general, will be a two-step process. Firstly, a surgeon, interventionist or other surgical or medical personnel would measure the length of the stenosis, and the diameter of the bore extending through the stenosis, as well as the diameter of the non-diseased part 104 and 106 of the artery adjacent the respective opposite ends of the stenosis. A stent 1 according to the invention of suitable dimensions would then be selected. In the absence of a suitably dimensioned stent 1, a stent 1 according to the invention of suitable dimensions would be manufactured.

In this embodiment of the invention the stenosis 102 is formed by plaque on the arterial wall 101 of the artery 100. The diameter d of a bore 103 extending through the stenosis 102 is approximately 0.6 mm.

The length L of the stenosis 102 is approximately 5 mm. The diameter D of the proximal and distal non-diseased parts 104 and 106, respectively, of the artery 100 adjacent respective proximal and distal ends 105 and 107, respectively, of the stenosis 102 is approximately 3 mm.

Accordingly, in this embodiment of the invention the stent 1 is configured to expand when placed in situ in the stenosis 102 so that the external diameter $d_1$ of the central portion 5 is approximately 1.5 mm and the external diameters $D_1$ of the first and second end portions 3 and 4 are equal to each other and are approximate 3.5 mm. The axial length $L_1$ of the central portion 5 in the expanded state of the stent 1 is approximately 5 mm, while the axial length $L_2$ of the first and second end portions 3 and 4 in the expanded state of the stent 1 in this embodiment of the invention are equal to each other and in this embodiment of the invention are approximately 2 mm. It will be appreciated that the axial lengths of the first and second end portions 3 and 4 of the stent 1 may be the same or different.

As mentioned above the dimensions of the stent 1 in the expanded state are largely dependent on the dimensions of the artery and the stenosis thereof and are chosen to be suitable for the particular stenosis. However, typically, in the expanded state the external diameter $d_1$ of the central portion 5 of the stent 1 would range between 1 mm and 3 mm, and more typically would lie within the range of 1.2 mm to 2.5 mm. The external diameter $D_1$ of the first and second end portions 3 and 4 of the stent 1 in the expanded state, in general, would lie within the range of 2 mm to 5 mm, and more typically would lie in the range of 2.5 mm to 4.5 mm. Additionally, the length $L_1$ of the central portion 5 of the stent 1 in the expanded state of the stent would typically lie in the range of 5 mm to 20 mm, and more typically, would lie in the range of 5 mm to 15 mm. The axial length $L_2$ of each of the first and second end portions 3 and 4 of the stent 1 in the expanded state thereof typically would lie in the range of 2 mm to 4 mm, and more typically would lie in the range of 2 mm to 3 mm, and may be of the same or different axial lengths.

In order that the stent 1 in the unexpanded state can be manoeuvred through the intracranial vascular system to the stenosis 102 in the artery 100, in general, in the unexpanded state, the stent 1 would be of substantially constant external diameter $d_3$ along its entire axial length $L_3$, of not more than 0.6 mm, and the axial length $L_3$ of the stent 1 in the unexpanded state, in general, would not exceed 30 mm, see FIG. 5. Although, depending on the location of the artery or vessel and the stenosis thereof in the intracranial vascular system, the maximum external diameter $d_3$ of the stent 1 in the unexpanded state would not exceed 0.5 mm. Ideally, the stent 1 in the unexpanded state would be of maximum external diameter $d_3$ not exceeding 0.4 mm, and of length $L_3$ not exceeding 25 mm.

The relationship between the external diameter $d_1$ of the central portion 5 and the external diameter $D_1$ of the first and second end portions 3 and 4 in the expanded state of the stent 1 are chosen so that the radial outward pressure exerted by the central portion 5 on the stenosis 102 is sufficient in order to maintain the diameter of the bore 103 extending through the stenosis 102 to be at least 25% of the diameter of the proximal and distal non-diseased parts 104 and 106 of the artery 100 adjacent the proximal and distal ends 105 and 107 of the stenosis 102, and the radial outward pressure exerted by the first and second end portions 3 and 4 on the proximal and distal non-diseased parts 104 and 106 of the wall 101 of the artery 100 adjacent the respective proximal and distal ends 105 and 107 of the stenosis 102 is sufficient to anchor the stent 1 in the artery 100 against the arterial wall 101 thereof. The pressure exerted by the first and second end portions 3 and 4 on the arterial wall 101 may also be sufficient in many cases to prevent the material forming the stenosis 102 being squeezed longitudinally along the wall 101 of the artery 100 between the first and second end portions 3 and 4 and the wall 101 of the artery 100 from the stenosis 102.

The external diameter $d_i$ of the central portion 5 of the stent 1 in the expanded state is chosen to apply a radial outward pressure to the stenosis to increase the diameter of the bore 103 through the stenosis 102 to a diameter in the range of 25% to 60%, and in some cases up to 75% and even 80% of the diameter of the proximal and distal non-diseased parts 104 and 106 of the artery 100 adjacent the proximal and distal ends 105 and 107, respectively, of the stenosis 102. Although ideally, the external diameter of the central portion 5 in the expanded state is such as to apply a sufficient radial outward pressure to the stenosis 102 to increase the diameter of the bore 103 therethrough to approximately 50% of the diameter of the proximal and distal non-diseased parts 104 and 106 of the artery 100 adjacent the proximal and distal ends 105 and 107, respectively, of the stenosis 102.

Additionally, and in general, the external diameter $d_1$ of the central portion 5 in the expanded state of the stent 1 is chosen so that the radial outward pressure applied by the central portion 5 of the stent 1 in its expanded state to the stenosis 102 is sufficient to increase the diameter of the bore 103 extending through the stenosis 102 to a diameter, such that the blood flow rate through the artery 100 is increased to a value greater than 50% of the normal blood flow rate through the artery prior to the formation of the stenosis. Since resistance to flow is inversely related to the fourth power of the internal diameter of a conduit, the external diameter of the central portion 5 in the expanded state of the stent 1 is selected based on this relationship in order to restore the blood flow rate through the bore 103 of the stenosis 102 to 50% or greater than that of the normal blood flow rate. This, it has been found, is sufficient to maintain the blood flow to the downstream tissue being supplied by the diseased artery 100 to protect the downstream tissue from hypoxia, ischemia and/or infarction while maintaining the downstream tissue in an oligemic state, and is also sufficient to promote the natural intracranial angiogenesis process until it has been completed and new collateral blood vessels have been grown to supply the sites supplied by the diseased artery. However, in some embodiments of the invention it is envisaged that the external diameter of the central portion 5 of the expanded stent 1 may be such as to lightly bear on the stenosis 102 in order to maintain the blood flow through the artery at the current flow rate or slightly above the current flow rate, depending on the current flow rate, which may be sufficient to protect the downstream tissue from hypoxia, ischemia and/or infarction while maintaining the downstream tissue in an oligemic state.

In general, the radial outward pressure applied to the stenosis 102 by the central portion 5 is greater than the radial outward pressure applied by the first and second end portions 3 and 4 to the wall 101 adjacent the proximal and distal non-diseased parts 104 and 106 of the artery 100 in the expanded state of the stent 1. However, the central portion 5 is configured so that the maximum transverse cross-sectional area to which the central wall 15 can expand is limited to a predefined maximum transverse cross-sectional area, which is chosen to be less than the transverse cross-sectional area of the proximal and distal non-diseased parts 104 and 106 of the artery 100, adjacent the stenosis 102. This is to ensure that the central wall 15 of the central portion 5 in the expanded state of the stent 1 is spaced apart from the arterial wall 101 of the artery 100, and does not come in contact with the arterial wall 101 of the non-diseased part of the artery 100 adjacent the stenosis 102.

The stent 1 in this embodiment of the invention is formed from a perforated material which is perforated to form struts 23 suitably connected to form interstices 20 therebetween extending through the material. In this embodiment of the invention the material of the stent 1 comprises a memory metal, so that the stent 1 is self-expanding and preferably, expands at the normal blood temperature in the human or animal body. While many metals and other materials may be used to provide such a self-expanding stent, in this embodiment of the invention the material of the stent is a nickel titanium alloy known as Nitinol. In the unexpanded state of the stent 1, the stent 1 is radially compressed so that the struts 23 lie adjacent each other, and depending on the pattern of the perforations which form the stent 1, the struts 23 in the compressed unexpanded state of the stent 1 may extend in an axial direction.

The interstices 20a extending through the central wall 15 of the central portion 5 in the expanded state of the stent 1 are of area less than the area of the interstices 20b extending through the first and second walls 10 and 11 of the first and second end portions 3 and 4. The interstices 20c extending through the transition walls 17 of the transition portions 7 are of area substantially similar to the area of the interstices 20a extending through the central wall 15 of the central portion 5. In this embodiment of the invention the interstices 20a and 20c extending through the central wall 15 of the central portion 5 and the transition walls 17 of the transition portions 7 in the expanded state of the stent 1 are of sufficiently small area in order to at least minimise and preferably prevent the material forming the stenosis 102 penetrating through the interstices 20a and 20c in the central portion 5 and the transition portions 7. Additionally, by providing the interstices 20a and 20c of the central portion 5 and the transition portions 7 to be of area smaller than the interstices 20b of the first and second end portions 3 and 4, results in the radial outward pressure exerted on the stenosis 102 by the central portion 5 being greater than the radial outward pressure exerted on the proximal and distal parts 104 and 106 of the artery 100 by the first and second end portions 3 and 4.

The wall thickness of the first and second walls 10 and 11 of the first and second end portions 3 and 4 is similar to the wall thickness of the central wall 15 of the central portion 5. Accordingly, in the expanded state of the stent 1 the relationship between the internal diameter $d_2$ of the central wall 15 of the central portion 5 and the internal diameter $D_2$ of the first and second walls 10 and 11 of the first and second end portions 3 and 4 is substantially similar to the relationship between the external diameter $d_1$ of the central wall 15 of the central portion 5 and the external diameter $D_1$ of the first and second walls 10 and 11 of the first and second end portions 3 and 4. In this embodiment of the invention the wall thickness of the first and second end walls 10 and 11, the central wall 15 and the transition walls 17 is approximately 0.1 mm. However, it is envisaged that the thickness of the first and second end walls, the central wall and the transition walls may lie in the range between 0.02 mm and 0.1 5 mm, although preferably, the thickness of the first and second end walls, the central wall and transition walls will ideally lie in the range of 0.05 mm to 0.1 mm. The selection of the thickness of the first and second end walls, the central wall and the transition walls will be chosen to optimise between the strength and function of the stent on the one hand, and minimising endothelial shear stress resulting from the use of the stent on the other hand. In general, the wall thickness of the stent will be selected so that the endothelial shear stress does not exceed 250 Pa.

In this embodiment of the invention the stent is configured so that in the expanded state of the stent the external diameter of the first and second end portions 3 and 4 of the stent is approximately 110% of the diameter of the proximal and distal non-diseased parts 104 and 106 of the artery adjacent the proximal and distal ends 105 and 107, respectively, of the stenosis 102. However, it is envisaged that the external diameter of the first and second end portions 3 and 4 of the stent 1 may be configured to expand in the expanded state of the stent to a diameter lying in the range of 100% to 125% of the diameter of the proximal and distal non-diseased parts 104 and 106 of the artery adjacent the proximal and distal ends 105 and 107, respectively, of the stenosis 102, and preferably, in the range of 100% to 110% of the diameter of the artery in the proximal and distal non-diseased parts 104 and 106 thereof.

The stent 1 is coated with a therapeutically active material, and in this embodiment of the invention is coated with two therapeutically active materials, one of which comprises an angiogenesis promoting material, and the other of which prevents further growth of plaque. Typically, the angiogenesis promoting material comprises methacrylic acid-ecoisodecyl acrylate (MAA-co-IDA; 40% MAA). The therapeutically active material for preventing further growth of plaque may comprise any one or more of the sirolimus and paclitaxel.

Referring now to FIGS. 7 to 9 there is illustrated a delivery system 30 for delivering the stent 1 to the stenosis 102 in the artery 100. The delivery system 30 comprises a delivery microcatheter 31 extending between a proximal end 32 and a distal end 33. An elongated bore 34 extends through the delivery microcatheter 31 from the proximal end 32 to the distal end 33 for accommodating delivery of the stent 1 therethrough to the stenosis 102 when the distal end 33 of the delivery microcatheter 31 is located in the stenosis 102 and projects distally from the stenosis, see FIG. 7. The bore 34 is of diameter such that the stent 1 in its unexpanded state is freely slideable through the bore 34, and will vary depending on the diameter of the stent in the unexpanded state, and typically will be in the range of 0.68 mm to 0.84 mm. The outer diameter of the delivery microcatheter 31 is such that the delivery microcatheter 31 is urgeable through the intracranial vascular system to and through the bore 103 of the stenosis 102 from a suitable entry point, which typically, may be the femoral, radial, brachial or carotid arteries. Additionally, the delivery microcatheter 31 is of sufficient flexibility in order to facilitate negotiating the delivery microcatheter 31 through the intracranial vascular system to the stenosis 102 in the artery 100.

An elongated positioning member 40 of diameter less than the diameter of the bore 34 of the delivery microcatheter 31 is provided for delivering the stent 1 through the delivery bore 34 of the delivery microcatheter 31 to the stenosis 102 in the artery 100. The positioning member 40 extends between a proximal end 41 and a distal end 42 and terminates at its distal end 42 in a releasable coupling mechanism 44 for releasably coupling the positioning member 40 to the stent 1 adjacent the free end 19 of the first wall 10 of the first end portion 3. The first end portion 3 of the stent 1 is configured for locating in the proximal non-diseased part 104 of the artery 100 adjacent a proximal end 105 of the stenosis 102, while the second end portion 4 is configured for locating in the distal non-diseased part 106 of the artery 100 adjacent a distal end 107 of the stenosis 102. In this embodiment of the invention the coupling mechanism 44 for coupling the free end 19 of the first wall 10 of the first end portion 3 to the positioning member 40 is a conventional coupling mechanism, which will be known to those skilled in the art, and is operable from the proximal end 41 of the position member 40 for releasing the stent 1 from the positioning member 40 when the stent 1 has been correctly positioned in the stenosis 102. Alternatively, the coupling mechanism may be releasably coupled to the free end 19 of the second end wall 11 of the second end portion 4.

In use, typically, the procedure for delivering the stent 1 to the stenosis 102 in the artery 100, commences with a guide wire (not shown) being entered into the intracranial vascular system, typically, through the femoral, radial, brachial or carotid arteries. The guide wire is urged from the entry point into the intracranial vascular system, and is urged through the intracranial vascular system to the stenosis 102 in the artery 100. The guide wire is urged through the bore 103 in the stenosis 102 so that a distal end of the guide wire extends into the artery 100 distally of the distal end 107 of the stenosis 102. The delivery microcatheter 31 is then urged over the guide wire through the intracranial vascular system until the distal end 33 of the delivery microcatheter 31 extends through the bore 103 extending through the stenosis 102 to the distal non-diseased part 106 of the artery 100 adjacent the distal end 107 of the stenosis 102. The guide wire is then withdrawn through the bore 34 of the delivery microcatheter 31.

The stent 1 in its unexpanded state is coupled to the positioning member 40 adjacent the distal end 42 by the coupling mechanism 44. With the stent 1 in its unexpanded state coupled to the distal end 42 of the positioning member 40, the positioning member 40 urges the stent 1 into the bore 34 of the delivery microcatheter 31 adjacent the proximal end 32 thereof with the second end portion 4 leading the stent 1. The stent 1 is then urged through the bore 34 of the delivery microcatheter 31 to the distal end 33 thereof by the positioning member 40. When the stent 1 is within the bore 34 of the delivery microcatheter 31 adjacent the distal end 33 thereof, the leading portion of the stent 1, namely, the second end wall 10 of the second end portion 4 is exposed by slightly withdrawing the delivery microcatheter 31 proximally. The second end wall 11 of the second end portion 4 of the stent 1 on being exposed and coming in contact with the blood at the normal body temperature of the subject commences to expand in the distal non-diseased part 106 of the artery adjacent the distal end 107 of the stenosis 102, see FIG. 8.

The position of the stent 1 is adjusted by appropriately manoeuvring the delivery microcatheter 31 and the positioning member 40 simultaneously in order to correctly position the second wall 11 of the second end portion 4 in its correct position in the distal non-diseased part 106 of the artery 100 adjacent the distal end 107 of the stenosis 102. Once the second wall 11 of the second end portion 4 is correctly positioned in the distal non-diseased part 106 of the artery 100 adjacent the distal end 107 of the stenosis 102, the delivery microcatheter 31 is further proximally withdrawn in order to completely expose the stent 1.

The remainder of the stent 1 on coming in contact with the blood in the artery 100 at body temperature expands with the central wall 15 of the central portion 5 located in the bore 103 of the stenosis 102 bearing on the stenosis 102, and the first wall 10 of the first end portion 3 bearing on the proximal non-diseased part 104 of the artery 100 adjacent the proximal end 105 of the stenosis 102. The material forming the stenosis 102 is completely contained within an annulus 108 defined by the central wall 15 of the central portion 5, the transition walls 17 of the transition portions 7 and the portion of the wall 101 of the artery 100 adjacent the stenosis 102.

The positioning member 40 is decoupled from the stent 1 by decoupling the coupling mechanism 44 from the stent 1. The positioning member 40 and the delivery microcatheter 31 are withdrawn through the intracranial vascular system and in turn through the femoral, radial, brachial or carotid arteries as the case may be.

With the stent 1 in its expanded state in the stenosis 102 the material forming the stenosis 102 is retained in the annulus 108 by the central wall 15 of the central portion 5 and the transition walls 17 of the transition portions 7 and by the action of the first and second walls 10 and 11 of the first and second end portions 3 and 4 bearing on the proximal and distal non-diseased parts 104 and 106 of the artery 100 adjacent the proximal and distal ends 105 and 107 of the stenosis 102. The action of the first and second walls 10 and 11 of the first and second end portions 3 and 4 on the proximal and distal non-diseased parts 104 and 106 retain the stent 1 firmly anchored in the artery 100, and also prevent the material forming the stenosis 102 being urged between the wall 101 of the artery 100 and the first and second walls 10 and 11 of the first and second end portions 3 and 4. The central wall 15 of the central portion 5 bears on the stenosis 102 to either maintain the diameter of the bore 103 extending through the stenosis 102 at its diameter prior to placing the stent 1 in the stenosis 102, or to increase the diameter of the bore 103 extending through the stenosis 102 to a diameter sufficient to maintain the flow rate of blood through the artery 100 at or greater than 50% of the normal flow rate of the blood therethrough prior to the formation of the stenosis 102 therein. By maintaining the flow rate of the blood through the artery 100 at or greater than 50% of the normal flow rate, the downstream tissue is protected from hypoxia, ischemia and infarction while maintaining the downstream tissue oligemic state. Thus, the natural intracranial angiogenesis process is promoted whereby new and collateral blood vessels are grown to provide a blood supply to the downstream tissue supplied by the diseased artery 100.

The provision of the therapeutically active intracranial angiogenesis material coated onto the stent further enhances the natural intracranial angiogenesis process, and the therapeutically active material coated onto the stent for preventing further growth of plaque, prevents or at least minimises any further growth of plaque.

Referring now to FIG. 10 there is illustrated a stent according to another embodiment of the invention indicated generally by the reference numeral 50. The stent 50 is substantially similar to the stent 1, and similar components are identified by the same reference numerals. The stent 50 in this embodiment of the invention is also particularly suitable for stenting a intracranial artery, such as the artery 100 having a stenosis 102 therein, for maintaining or increasing the rate of blood flow through the stenosis 102 to protect downstream tissue from hypoxia, ischemia and/or infarction while maintaining the downstream tissue in an oligemic state, for in turn promoting natural intracranial angiogenesis. The dimensions of the stent 50 are within the dimensional ranges discussed with reference to the stent 1. The main difference between the stent 50 and the stent 1 lies in the transition portions 7. In this embodiment of the invention instead of the transition portions 7 being formed by a transition wall 17 extending perpendicularly from the central wall 15 of the central portion 5 and extending perpendicularly from the first and second walls 10 and 11 of the first and second end portions 3 and 4, the transition portions 7 of the stent 50 are formed by frusto-conical wall portions 52, which in turn are formed by transition walls 53 which diverge outwardly from the central wall 15 of the central portion 5 to the first and second walls 10 and 11 of the first and second end portions 3 and 4, respectively.

The wall thickness of the transition walls 53 is substantially similar to the wall thickness of the first and second walls 10 and 11 and the central wall 15 of the first and second end portions 3 and 4 and the central portion 5, respectively. The external diameter of the transition walls 53 adjacent the central wall 15 of the central portion 5 is similar to the external diameter $d_1$ of the central wall 15. The internal diameter of the transition walls 53 adjacent the central wall 15 of the central portion 5 is similar to the internal diameter $d_2$ of the central wall 15 of the central portion 5. The external diameter of the transition walls 53 adjacent the first and second walls 10 and 11 of the first and second end portions 3 and 4 is similar to the external diameter $D_1$ of the first and second walls 10 and 11 of the first and second end portions 3 and 4, while the internal diameter of the transition walls 53 adjacent the first and second walls 10 and 11 of the first and second end portions 3 and 4 is similar to the internal diameter $D_2$ of the first and second walls 10 and 11 of the first and second end portion 3 and 4.

In this embodiment of the invention the cone angle defined by the frusto-conical transition walls 53 is approximately 60°. This, thus, results in the external diameter of each transition wall 53 increasing from the central wall 15 to the corresponding one of the first and second walls 10 and 11 at a rate of approximately 1.72 mm per 1 mm of length from the central wall 15.

In this embodiment of the invention the stent 50 also comprises a memory alloy know as Nitinol, and is formed of perforated construction having interstices 20. The interstices 20a and 20c extending through the central wall 15 and the transition walls 53 are of area less than the area of the interstices 20b extending through the first and second walls 10 and 11 of the stent 50. In this embodiment of the invention the area of the interstices 20a and 20c extending through the central wall 15 and the transition walls 53 is such as to minimise, and in general, prevent the material forming the stenosis 102 penetrating through the central wall 15 and the transition walls 53.

In this embodiment of the invention the stent 50 is also coated with a therapeutically active intracranial angiogenesis promoting material, and a therapeutically active material for preventing the growth of plaque.

Use of the stent 50 and the delivery of the stent 50 to the stenosis 102 of the artery 100 is similar to that already described with reference to the use and delivery of the stent 1 to the stenosis 102 of the artery 100. However, in this embodiment of the invention when the stent 50 has been urged through the bore 34 of the delivery microcatheter 31 by the positioning member 40, the delivery microcatheter 31 is urged proximally to expose both the second end wall 11 and the adjacent transition wall 53 thereby permitting the second wall 11 and the adjacent transition wall 53 to expand on coming into contact with the blood in the artery 100 of the subject, so that the second wall 11 of the stent 50 engages and bears on the distal non-diseased part 106 of the artery 100 distally of the stenosis 102. However, thereafter the manoeuvring of the delivery microcatheter 31 and the positioning member 40 to accurately position the stent 50 in the stenosis 102 is similar to that described with reference to delivery and positioning of the stent 1.

Referring now to FIG. 11 there is illustrated a stent according to another embodiment of the invention indicated generally by the reference numeral 60. The stent 60 is substantially similar to the stent 1, and similar components are identified by the same reference numerals. The stent 60 in this embodiment of the invention is also particularly suitable for stenting a intracranial artery, such as the intracranial artery 100 having a stenosis 102 therein for maintaining or increasing the rate of blood flow through the stenosis 102 to protect downstream tissue from hypoxia, ischemia and/or infarction while maintaining the downstream tissue in an oligemic state, for in turn promoting natural intracranial angiogenesis. The dimensions of the stent 60 are within the dimensional ranges discussed with reference to the stent 1. The only difference between the stent 60 and the stent 1, is that in the stent 60, the central portion 5 is of "hourglass" shape having a minimum external diameter $d_1$. Transition portions 7 extending from the central portion 3 are of frusto-conical shape, similar to the transition portions 7 of the stent 50. In this embodiment of the invention the area of the interstices 20a and 20c of the central portion 5 and the transition portions 7 are of area smaller than the area of the interstices 20b of the first and second end portions 3 and 4. Additionally, in this embodiment of the invention the area of the interstices 20a and 20c of the central portion 5 and the transition portions 7 is such as to at least minimise, and preferably, prevent material forming the stenosis 102 extending through the interstices 20a and 20c in the central portion 5 and the transition portions 7.

Otherwise the stent 60 and its use is substantially similar to that described with reference to the stent 1, and is of dimensions within the ranges discussed in connection with the stent 1.

Referring now to FIG. 12 there is illustrated a stent according to a further embodiment of the invention indicated generally by the reference numeral 70. The stent 70 is substantially similar to the stent 1, and similar components are identified by the same reference numerals. The stent 70 in this embodiment of the invention is also particularly suitable for stenting a diseased artery, for example, the artery 100 having a stenosis 102 therein, for maintaining or increasing the rate of blood flow through the stenosis 102 to protect downstream tissue from hypoxia, ischemia and/or infarction while maintaining the downstream tissue in an oligemic state, for in turn promoting natural angiogenesis. The diameter dimensions of the stent 70 are within the diameter dimensional ranges discussed with reference to the stent 1. However, in this case a perforator artery 109 is branched off from the artery 100 at a location adjacent the stenosis 102. In this embodiment of the invention the length $L_1$ of the stent 70 between the first and second end portions 3 and 4, including the central portion 5 and the transition portions 7 is of sufficient length so that the first and second end portions 3 and 4 engage the proximal and distal non-diseased parts 104 and 106 of the artery such that both the stenosis 102 and the connection of the perforator artery 109 are contained within the annulus 108 defined between the central portion 5, the transition portions 7 and the wall 101 of the artery 100 adjacent the stenosis 102.

In this embodiment of the invention the radial outward pressure exerted by the central portion 5 on the stenosis 102 is such as to maintain the rate of the blood flow through the artery 100 at approximately 50% of the normal blood flow rate through the artery 100 prior to the formation of the stenosis 102. However, the radial outward pressure exerted by the central portion 5 on the stenosis 102 is such as to prevent excessive squashing of the material forming the stenosis 102 between the central portion 5 and the arterial wall 101 to the extent that the material of the stenosis would extend longitudinally along the arterial wall 101, and would have resulted in blocking of the perforator artery 109. In this embodiment of the invention while the area of the interstices 20a of the central portion 5 and the interstices 20c of the transition portions 7 is such as to prevent material forming the stenosis 102 extending therethrough, the area of the interstices 20a and 20c extending through the central portion 5 and the transition portions 7 is such as to permit blood flow through the central portion 5 and the transition portions 7 to the perforator artery 109.

Referring now to FIG. 13 there is illustrated a stent according to another embodiment of the invention indicated generally by the reference numeral 80, which is also suitable for urging through an intracranial vascular system to a stenosis 102 in an intracranial artery 100 in order to maintain the diameter or to increase the diameter of the bore 103 through the stenosis 102 for maintaining or increasing the rate of blood flow through the stenosis 102 to protect downstream tissue from hypoxia, ischemia and/or infarction while maintaining the downstream tissue in an oligemic state, for in turn promoting and supporting a natural intracranial angiogenesis process. In this embodiment of the invention the stent 80 is not of a self-expanding material, and accordingly, is configured for delivery to the stenosis 102 by a balloon microcatheter 82. The balloon microcatheter 82 comprises an elongated microcatheter 83 terminating at its distal end 84 in a balloon 85. The balloon 85 is appropriately shaped so that when inflated it inflates to take up the approximate shape of the stenosis 102 and the proximal and distal non-diseased parts 104 and 106 of the artery 100. The stent 80 when expanded by the balloon 85 in the stenosis 102 is configured to take up a shape substantially similar to that of the stent 50, whereby the stent 80 when expanded by the balloon 85 comprises first and second end portions 3 and 4, a central portion 5 of diameter less than the diameter of the first and second end portions 3 and 4, and respective frusto-conical transition portions 7 extending from the central portion 5 to the first and second end portions 3 and 4. The material of the stent 80, is such that once expanded by the balloon 85 in the stenosis 102, the stent 80 retains its expanded shape, thereby maintaining the bore 103 extending through the stenosis 102 at a diameter in order to provide a blood flow rate through the stenosis 102 of approximately 50% of the normal flow rate through the artery 100 prior to the formation of the stenosis 102. The material of the stent is of perforated construction having interstices 20 extending through the first and second end portions 3 and 4, the central portion 5 and the transition portions 7. The interstices 20a and 20c extending through the central portion 5 and the transition portions 7 are smaller than the interstices extending through the first and second end portions 3 and 4, as already described with reference to the stent 1.

Delivery of the stent 80 to the stenosis 102 is substantially similar to the delivery of the stent 1 to the stenosis 102 as already described with reference to FIGS. 7 to 9, with the exception that instead of delivering the stent 80 through the delivery microcatheter 31 by a positioning member 40, the stent 1 in the unexpanded state is delivered through the delivery microcatheter 31 on the balloon microcatheter 82. The stent 80 in its unexpanded state is located on the balloon 85 in its deflated state, and is delivered through the delivery microcatheter 31 to the stenosis 102. On the balloon 85 with the stent 80 thereon in its unexpanded state being located in the stenosis 102, the balloon 85 is inflated to in turn expand the stent 80 in the stenosis 102, with the central portion 5 of the stent 80 bearing on the stenosis 102, and the first and second end portions 3 and 4 of the stent 80 bearing on and engaging the proximal and distal non-diseased parts 104 and 106 of the artery 100. On completion of the positioning of the stent 80 in the stenosis 102, the balloon 85 is deflated and withdrawn along with the delivery microcatheter as already described with reference to FIGS. 7 to 9.

Referring now to FIGS. 14a, b and c to FIGS. 17a, b and c, there is illustrated four expandable stents according to further embodiments of the invention indicated generally by the reference numerals 90 to 93, respectively, for use in a human or animal subject, for opening, or at least maintaining a stenosis open in a diseased artery in the intracranial vascular system, for maintaining or increasing the rate of blood flow through the stenosis 102 to protect downstream tissue from hypoxia, ischemia and/or infarction while maintaining the downstream tissue in an oligemic state, for in turn promoting a natural intracranial angiogenesis process. The expandable stents 90 to 93 are substantially similar to the expandable stent 1 described with reference to FIGS. 2 to 6, and similar components are identified by the same reference numerals. The main difference between the stents 90 to 93 and the stent 1 is that, in the expanded state of each of the stents 90 to 93 the central portion 5 of each of the stents 90 to 93 is eccentrically located relative to the first and second end portions 3 and 4 thereof. In other words, a main central axis 95 defined by the central portion 5 of each stent 90 to 93 is offset from first and second central axes 96 and 97 defined by the first and second end portions 3 and 4 of the corresponding one of the stents 90 to 93. In this embodiment of the invention the first and second end portions 3 and 4 of the stents 90 to 93 are axially aligned with each other, and therefore the first and second central axes 96 and 97 coincide with each other. However the main central axis 95 of the central portion 5 of each stent 90 to 93 extends parallel to the first and second central axes 96 and 97 of the first and second end portions 3 and 4 of the corresponding one of the stents 90 to 93, and is transversely offset from the first and second central axes 96 and 97 thereof. Although, it is envisaged that the main central axis 95 of the central portion 5 in some cases may extend at an angle relative to the first and second central axes 96 and 97 of the first and second end portions 3 and 4 of the corresponding stent 90 to 93. The stents 90 to 93 are particularly suitable for use in a diseased intracranial artery in which the stenosis is located asymmetrically in the diseased artery.

In the stents 90 and 91, the transition portions 7 extend perpendicularly from the central portion 5 and also extend perpendicularly from the first and second end portions 3 and 4. In the stents 92 and 93, the transition portions 7 are formed by transition walls 17, which are of asymmetric frusto-conical shape. Additionally, in the stents 90 and 92 of FIGS. 14*a, b* and *c*, and 16*a, b* and *c*, respectively, the central wall 15 of the central portion 5 and the first and second end walls 10 and 11 of each of the stents 90 and 92 run tangentially to each other along one side of the stent.

The dimensions of the stents 90 to 93 lie within ranges similar to the dimensional ranges discussed with reference to the stent 1 described with reference to FIGS. 2 to 6. Additionally, the stents 90 to 93 may or may not be coated with a therapeutically active material as described with reference to the stent 1.

Use and delivery of the stents 90 to 93 to a stenosis in the intracranial vascular system is similar to that already described with reference to the stent 1 with reference to FIGS. 2 to 9. Otherwise, the stents 90 to 93, their use and delivery are similar to the stent 1.

Referring now to FIG. 18 there is illustrated a stent according to another embodiment of the invention indicated generally by the reference numeral 200 which is also suitable for advancement through a delivery microcatheter placed in the intracranial vascular system to a stenosis similar to the stenosis 102 in an intracranial artery similar to the intracranial artery 100 in order to achieve a threshold level of dilation to the bore 103 through the stenosis 102 to maintain blood flow through the stenosis 102 in order to prevent hypoxia, ischemia of infarction and to promote and support a natural intracranial angiogenesis process. The stent 200 is substantially similar to the stent 1, with the exception that the transition portions 7 are formed by frusto-conical portions, and for convenience similar components to those of the components of the stent 1 are identified by the same reference numerals. In FIG. 18 the stent 200 is illustrated with a support element extending through the stent 200. The support element does not form a part of the stent 200.

In this embodiment of the invention the stent 200 is of a self-expanding stent made from a nitinol material compris-
ing struts 23 connected at crowns 201 which define interstices 20 therebetween, the stent 200 comprises a highly polished surface finish. It will be noted with reference to FIG. 18 that the stent comprises a first portion 3, a second portion 4 and a central portion 5 similar to the embodiments described with reference to the stents of 1, 50, 60, 70 and 80. In this embodiment the stent 200 comprises transition portions which are of frusto-conical shape defining a cone angle of approximately 110°. The crowns 201 comprise V or U shaped elements in the stent pattern and the struts 23 interconnect the crowns 201.

The stent 200 further comprises a plurality of ring structures, in this embodiment of the invention seven ring structures. Each ring structure comprises a plurality of interconnected struts 23 and crowns 201 organised to form a tubular ring around the main and first and second central axes 18, 21 and 22, which in this embodiment of the invention coincide. Adjacent rings are connected together with connectors. In one embodiment the connectors are configured such that adjacent rings are spaced apart from each other. In another embodiment the crowns 201 of a first ring interpenetrate with the crowns 201 of an adjacent ring.

The stent 200 has an expanded state and a collapsed state. In the fully expanded state the stent 200 is stress free. The stent 200 is compressed, and thus stressed, in order for it to assume the collapsed state for delivery. In the expanded state the V angle Θ of the crowns 201 is large and in the collapsed state the V angle Θ of the crowns 201 is small. Indeed the V angle Θ of the crowns 201 is less than 5° in the collapsed state. In contrast the V angle Θ of the crowns 201 is relatively larger in the expanded state. Preferably the V angle Θ is greater than 40° in the expanded state. More preferably the V angle Θ is greater than 60° and even more preferably the V angle Θ is greater than 80°.

The stent 200 of this embodiment is designed to be conformable and to protect flow to perforators and branch vessels, such as the perforator vessel 109 in FIG. 12. The larger V angle in the expanded configuration is configured to be large to provide flow orifices formed by the interstices 20 between the struts 23. The struts 23 are configured to be short and narrow. Short and narrow struts while challenging to manufacture make the stent 200 more conformable and the narrow struts 23 maintain flow through the flow orifices formed by the interstices 20. In one embodiment the struts 23 are configured such that the length of at least one ring in the stent is less than 2 mm. In another embodiment the struts 23 are configured such that the length of at least one ring in the stent is less than 1.5 mm. In yet another embodiment the struts 23 are configured such that the length of at least one ring in the stent is less than 1.0 mm. In one embodiment the struts 23 are configured to be less than 80 micrometres wide. In another embodiment the struts 23 are configured to be less than 60 micrometres wide. In yet another embodiment the struts 23 are configured to be less than 40 micrometres wide.

In one embodiment at least one ring of the stent structure comprises six struts 23 with three pairs of opposing crowns 201. In another embodiment at least one ring of the stent structure comprises eight struts 23 with four pairs of opposing crowns 201. In another embodiment at least one ring of the stent structure comprises ten struts 23 with five pairs of opposing crowns 201. In another embodiment at least one ring of the stent structure comprises twelve struts 23 with six pairs of opposing crowns 201. In another embodiment at least one ring of the stent structure comprises fourteen struts 23 with seven pairs of opposing crowns 201. In another embodiment at least one ring of the stent structure comprises sixteen struts 23 with eight pairs of opposing crowns 201. In the embodiment of the stent 200 illustrated in FIG. 18 at least one ring of the stent structure comprises eighteen struts 23 with nine pairs of opposing crowns 201. In one embodiment the number of struts in a first ring is greater than the number of struts in an adjacent ring. In one embodiment the number of struts in a first ring is equal to the number of struts in an adjacent ring. In one embodiment the length of a first ring is greater than the length of a second adjacent ring.

The stent 200 of FIG. 18 is shape set to create an undulating tubular structure with a waisted section, namely, the central portion 5. In one embodiment the stent is cut from a nitinol tube using a laser process, deburred and grit blasted. The shape setting of the stent 200 comprises heating the stent to a temperature in excess of 400° centigrade for a number of minutes until the desired shape is programmed into the stent 200. The stent is cooled and the stent is electropolished to produce a surface with a highly polished finish.

In one embodiment the stent comprises a completely connected structure. In such an embodiment every crown of the stent is connected to an adjacent crown either directly or indirectly. The exception to this interconnectivity are those crowns that define the very distal and the very proximal ends of the stent. These crowns are not connected to adjacent crowns.

In another embodiment the stent 200 is configured for visualisation on fluoroscopy. In this embodiment a highly radiopaque metal is incorporated into the structure. The incorporation of the radiopaque metal allows the interventionalist to visualise the distal end of the stent which may be the first end portion 3 or the second end portion 4, the proximal end of the stent, which is the other one of the first and second end portions 3 or 4, the central portion 5 and the transition portions 7 between the central portion 5 and the first end portion 3 and second end portion 4.

In one embodiment the radiopaque element comprises gold, platinum, tantalum or tungsten. In another embodiment the incorporation of the radiopaque element comprises an alloy of Nitinol and the radiopaque element. In another embodiment the incorporation of the radiopaque element comprises the inclusion of a radiopaque marker into the structure of the stent. In one embodiment the radiopaque marker comprises a cylindrical slug of a radiopaque metal pressed into a plurality of laser drilled holes in the structure of the stent. Suitable radiopaque metals for use in said cylindrical slug include gold, platinum, tantalum, tungsten or alloys containing a substantial portion of one or more of these elements.

In one embodiment the central portion 5 of the stent 200 is configured to dilate the bore 103 of the stenosis 102 significantly without inducing a corresponding dilation in the vessel wall 100 in the region of the stenosis 102. The following examples of embodiments of stents similar to the stent 200 but of various dimensions and placed in stenoses 102 of various dimensions highlight this advantage of the invention.

EXAMPLE 1

Inputs

| | |
|---|---|
| Internal diameter D of the vessel 100 | 3 mm |
| External diameter $d_1$ of the central portion 5 of the stent 200 | 1.4 mm |
| External transverse cross-sectional area of the vessel 100 adjacent the stenosis 102 | 7.07 mm |
| External transverse cross-sectional area of the central portion 5 of the stent 200 | 1.54 mm$^2$ |
| Diameter d of the bore 103 extending through the stenosis 102 | 0.25 mm |
| Transverse cross-sectional area of the bore 103 extending through the stenosis 102 | 0.046 mm$^2$ |
| % occlusion by the stenosis 102 | 92% |

Calculations

| | |
|---|---|
| Increase in transverse cross-sectional area of the bore 103 extending through the stenosis 102 | 3036% |
| Transverse cross-sectional area of the stenosis annulus formed by the displaced material of the stenosis | 1.490 mm$^2$ |
| Diameter of the dilated vessel adjacent the stenosis | 3.30 mm |
| Increase in the vessel diameter adjacent the stenosis | 10% |

Conclusion

With a 92% stenosis the stent 200 of this example can increase the cross sectional area of the bore of the stenosis by over 3000%, while only dilating the vessel diameter by 10%.

EXAMPLE 2

Inputs

| | |
|---|---|
| Internal diameter D of the vessel 100 | 2.5 mm |
| External diameter $d_1$ of the central portion 5 of the stent 200 | 1.2 mm |
| External transverse cross-sectional area of the vessel 100 adjacent the stenosis 102 | 4.91 mm$^2$ |
| External transverse cross-sectional area of the central portion 5 of the stent 200 | 1.13 mm$^2$ |
| Diameter d of the bore 103 extending through the stenosis 102 | 0.3 mm |
| Transverse cross-sectional area of the bore 103 extending through the stenosis 102 | 0.071 mm$^2$ |
| % occlusion by the stenosis 102 | 88% |

Calculations

| | |
|---|---|
| Increase in transverse cross-sectional area of the bore 103 extending through the stenosis 102 | 1500% |
| Transverse cross-sectional area of the stenosis annulus formed by the displaced material of the stenosis | 1.060 mm$^2$ |
| Diameter of the dilated vessel adjacent the stenosis | 2.76 mm |
| Increase in the vessel diameter adjacent the stenosis | 10.3% |

Conclusion

With an 88% stenosis the stent 200 of this example can increase the cross sectional area of the bore of the stenosis by over 1500%, while only dilating the vessel diameter by 10.3%.

EXAMPLE 3

Inputs

| | |
|---|---|
| Internal diameter D of the vessel 100 | 2 mm |
| External diameter $d_1$ of the central portion 5 of the stent 200 | 1.1 mm |
| External transverse cross-sectional area of the vessel 100 adjacent the stenosis 102 | 3.14 mm$^2$ |
| External transverse cross-sectional area of the central portion 5 of the stent 200 | 0.95 mm$^2$ |

-continued

| | |
|---|---|
| Diameter d of the bore 103 extending through the stenosis 102 | 0.5 mm |
| Transverse cross sectional area of the bore 103 extending through the stenosis 102 | 0.196 mm² |
| % occlusion by the stenosis 102 | 75% |

Calculations

| | |
|---|---|
| Increase in transverse cross-sectional area of the bore 103 extending through the stenosis 102 | 384% |
| Transverse cross-sectional area of the stenosis annulus formed by the displaced material of the stenosis | 0.754 mm² |
| Diameter of the dilated vessel adjacent the stenosis | 2.23 mm |
| Increase in the vessel diameter adjacent the stenosis | 11.4% |

Conclusion

With a 75% stenosis the stent 200 of this example can increase the cross sectional area of the bore of the stenosis by over 384%, while only dilating the vessel diameter by 11.4%.

Accordingly, it can be seen from the above three examples that the stent 200 according to the invention of different dimensions when used in stenoses of different bore diameters can produce a significant increase in the stenosis bore transverse cross-section area for a relatively small increase in the diameter of the vessel resulting from the radial outward action of the central portion 5 of the stent 200 on the material forming the stenosis. Typically the increase in the transverse cross-sectional area of the bore extending through a stenosis can range from 300% to over 3000% for an increase in the diameter of the vessel adjacent the stenosis in the range of 10% to 12%.

In the embodiments of the invention where the stents have not been described as being coated with a therapeutically active material, in general, although not necessarily, but preferably, the stents according to the invention will be coated with a therapeutically active material. A preferred therapeutically active material with which the stents according to these embodiments of the invention will be coated is an angiogenesis promoting material. The stents according to the invention may be coated with any suitable angiogenesis promoting material, for example, methacrylic acid-ecoisodecyl acrylate (MAA-co-IDA; 40% MAA).

While the stents according to the invention have been described as comprising Nitinol, it is envisaged that the stents may comprise any suitable biocompatible material, such as stainless steel or cobalt alloy. By providing the stents to be of perforated construction, the quantity of metal in the stents is minimised, which has the advantage of reducing the thrombotic potential of the stents, and notably permits flow of blood from the stented artery to a perforator artery through the central wall, the transition walls and the first and second walls of the central, transition and first and second end portions, respectively, of the stent, as described in connection with the stent 80 of FIG. 13, in the case of a perforator artery branching from an artery adjacent a stenosis. The less material used in the stents, the lower the potential for material to encourage formation of thrombosis once implanted in an artery.

While the stents according to the invention have been described as comprising a memory metal, the stents may be of a non-memory metal, and furthermore, may be of a non-self-expanding material. For example, it is envisaged that the stents may be of a material which is a non-self-expanding material as in the case of the stent 80. Furthermore, it will be readily apparent to those skilled in the art that the stent 80 may be made of a self-expanding memory material.

While the stents according to the invention have been described for stenting a stenosis in an intracranial artery, the stents according to the invention may be used for stenting a stenosis in any intracranial vessel, such as a vein, lumen or other such intracranial blood vessel.

In other embodiments of the stents, a biocompatible film or membrane may be provided to at least one surface of the stents. The film or membrane may or may not be perforated.

The film or membrane may be a non-woven fabric made of plastic fibrils. It is bonded to, or forms a bond with, the walls of the stents. The film or membrane may also be made into a thin strand which can be woven into a lattice which is layered onto the stent. The membrane and/or the lattice may be deposited on the stents in a manner that is aligned with the struts of the stents, or alternatively in a non-aligned manner. In certain embodiments of the invention, the membrane may have a porous structure capable of accommodating pharmaceutical materials and releasing these materials into the surrounding vessels and plaque, under physiological conditions.

The membrane may optionally be implanted or coated with one or more pharmaceutical compositions or other compositions having a desirable effect on the properties of the stents. This addresses the challenge of coating the stents surfaces with pharmaceutical materials. These compositions can release medication over time into the surrounding tissues, vascular surface or plaques. Proliferation-inhibiting substances such as paclitaxel and rapamycin, for example, can be beneficial. Other examples are substances that prevent thrombosis, or prevent liquid embolic agents or glue from adhering to the membrane and/or the stents.

The film or membrane may be suitably made of a polymeric material, such as polyurethane, polytetrafluoroethylene, polyester, polyamide or polyolefin. These polymeric membranes are not easily attached to a stent. Conventionally, stent membranes are held mechanically against a vessel wall or plaque by the radial force of an expanding stent. However, in the present invention, the central portion of the stents do not contact the arterial wall. The stents according to the invention having a membrane made from a polymeric material which is not easily attached to the walls of the stent are provided with a suitable connection of the membrane to the stents, typically a mechanical connection. Connections of this type are also useful if the stents require re-sheathing into a microcatheter for adjustment or relocation of the stent to another area.

The membranes of the stents may be conveniently made by spraying onto the stent walls, provided the stent walls are compatible with the polymer as regards formation of suitable bonds, or by electrospinning of the non-woven fabric around the struts of the stents; by applying an electric current, the fibrils of the membrane are separated from a polymer solution and deposited on a substrate. The technique of electrospinning is well known in the art and will not be described in further detail here. The deposition causes the fibrils to agglutinate into a non-woven fabric. It can be formed into strands that can be woven, if so chosen. The fibrils generally have a diameter of from 100 to 1000 nm. Membranes produced by electrospinning are very thin and uniform in thickness and can easily form a bond with the stent walls. Such membranes are strong enough to withstand mechanical stress during compression of the stents into a deliverable state, and during maneuvering of the stents along and into tortuous vessels. Such membranes can be pierced easily, mechanically, as required, without creating an opening that gives rise to fractures or cracks. The thickness and length of the fibrils can be controlled by the electrospinning process. Examples of such membranes include poly(lactide-co-caprolactone) (PLCL) which can have a degradation time of 6-18 months; poly(caprolactone) (PCL) which can have a degradation time of 2-3 years; or stiffer materials such as polylactides (PLA), poly(lactide-co-glycosides) (PLGA), polyacrylonitrile (PAN) or polyurethane (PU).

The membrane can be composed of a single layer or multiple layers. Multiple layers may be produced by different methods, for example a first layer by electrospinning, a second by spray coating and a third by electrospinning. Active pharmaceutical or other agents can be implanted on one or several of these layers. The agent can be released by diffusion or by degradation or erosion of the layers of the membrane. Radiopaque substances may also be implanted in the membrane so that it is more easily visible to the techniques used during stent implantation. In particular, in order to further promote and support angiogenesis, the stent may be coated with methacrylic acid-ecoisodecyl acrylate (MAA-co-IDA; 40% MAA) or similar substances known to promote angiogenesis.

The membrane may be laced with graphene to improve its strength and flexibility. Additionally, or alternatively, the membrane may comprise a thin film Nitinol.

The stents may be made of a biodegradable material such that it has a limited lifespan. Polymer-based stents are conventionally based on poly(L-lactide) (PLLA), chosen because it is able to maintain a radially strong scaffold that breaks down over time into lactic acid, a naturally occurring molecule that the body can use for metabolism. Other polymers in development include tyrosine polycarbonate and salicylic acid.

While a specific delivery system has been described for delivering the stent 1 to a stenosis in a intracranial artery, other suitable delivery means may be used, for example, via a balloon catheter. The stents according to the invention are constructed to be inserted without requiring pre-dilatation of the vessel. However, in certain conditions, pre-dilation of the ICAS may be indicated in order to navigate a delivery microcatheter or balloon microcatheter past the stenotic focus. Similarly, the stents may be constructed so that post-dilatation (dilatation of the stent with a balloon after insertion) is not required. However, in certain instances, such as where there is heavily calcified atherosclerotic plaque, post-dilation may be advantageous. Therefore, the stents, whilst not of themselves requiring pre-dilation or post-dilation, is compatible with pre-dilatation and post-dilatation. Where the stent is not self-expanding, a further aspect of the invention is the provision of a shaped dilation balloon, which will cause the outer ends of the stent to be dilated to a greater extent than the inner section, so as to achieve a dilated stent shape with dimensions as previously described for the self-expanding stent, as described with reference to FIGS. 2 to 12 and 14 to 18.

The stents according to the invention have been described as comprising perforated expandable walls, such that they may be folded-up in the unexpanded state to form a low profile for delivery into the arterial system. A low profile configuration allows for delivery into the smaller intracranial vessels and arteries via smaller microcatheters. The configuration of the stents can be of an open, closed or woven stent design.

The structure of the stents is illustrated as a closed cell type. The cell construction of the stents cause the stent to be auto-expandable once inserted into an artery. The stents according to the invention assumes a dumbbell shape upon expansion.

The stents may be formed with a reattachment system so that they may be re-sheathed even when fully delivered, such that an operator may re-adjust the deployment until fully satisfied with the positioning of the stents, relative to the stenosis. Conventional electrolytic severance of an intravascular stent implant involves using an electrolytically corrodible structure on the end of a delivery wire at the connection between the delivery wire and the intravascular stent implant. Such a device can make use of the voltage applied to the intravascular implant serving as an anode for electro-thrombosis. Alternatively, a mechanical reattachment system may be employed.

Accurate deployment of stents may be obtained via appropriately positioned radio-opaque markers which are visible under x-ray fluoroscopy, as is known in the art. Optionally, markers may be provided at the proximal and distal ends of the central portion of the stents. Alternatively or additionally, the central portion of stents may be made more radio-opaque by the application of a gold coating to the struts of the stents. Likewise, the whole of the stents can be substantially coated with a radio-opaque marker such as gold. Needless to say, any other radio-opaque markers may be provided on the stents.

Where the stents are made of a biodegradable material, such that it has a limited lifespan, the stents remain in place until they dissolve. Anti-platelet therapy is frequently recommended for patients that have received a stent. In the case that the stents are biodegradable, anti-platelet medication can be discontinued after dissolution of the stent.

Where the stents are not biodegradable, they are left in place and provide a scaffolding over which endothelial cells will grow over time.

The stents are deployed over a stenotic area (as described above). A narrower central portion is located in the bore of the stenosis in order to maintain or increase the diameter of the bore of the stenosis to an extent that restores blood flow distally. The diameter of the central portion is sufficient to open the stenosis to restore blood flow but it does not open the stenosis fully, rather it achieves around 50% of the diameter of the healthy artery.

The relatively small diameter of the central portion of the stents according to the invention acts to minimise the amount of material from the stenosis that is pushed into adjacent unoccupied areas of the artery. Furthermore, the sub-maximal angioplasty achieved by the stents minimises the likelihood of fracturing the plaque of the stenosis, and therefore minimises the chance of distal vessel stenosis.

Conventional self-expanding stents are anchored in place by the outward force of the stent on vessel walls along the whole length of the stent. This outward force causes a significant amount of atherosclerotic debris to be pushed to the walls of the blood vessel. Atherosclerotic debris that is pushed against walls of the blood vessel can be forced into adjacent side branches or small vessels (snow-ploughing). The arterial structure in the brain is highly branched and the presence of many side branches can readily lead to snow-ploughing in the case where significant amounts of atherosclerotic debris are forced against arterial walls.

In use of the stents according to the invention, the two larger diameter first and second end portions bear against the arterial wall of the artery to stabilise and support the narrower central portion the function of which is to open the stenosis. The construction minimises the amount of plaque that is pushed along the arterial walls by the stents, since it is only the first and second end portions that contact the arterial walls.

The central portion of the stents is constructed to exert a higher outward radial force than that exerted by the first and second end portions.

As discussed above, the provision of the central portion and the transition portions of the stents according to the invention being formed with relatively small interstices, minimises, and in general, prevents material from the stenosis being forced through the interstices in the central portion and the transition portions of the stents according to the invention. If material from the stenosis is forced through the interstices of the stents, small particles of plaque can be released from the stents back into the blood vessel; this is the so-called "cheese-grating" effect. These small plaque particles can float into the distal circulation, moving deeper into the brain vasculature, potentially causing distal emboli. By minimising the area of the interstices in the central and transition portions of the stents according to the invention, the "cheese-grating" effect is minimised.

Similarly, a dual layer construction for the stents according to the invention can be used to further decrease the "cheese-grating" effect of atherosclerotic plaque.

A biocompatible film or membrane can be provided to a surface of the stents, to further reduce the incidence of the "cheese-grating" effect, thereby minimising the release of distal emboli into the intracranial circulation.

The stents of the present invention provide an early stage, non-medical treatment for ICAS and reduce the complications associated with conventional stent treatments of ICAS by, for example, minimising plaque forced into interstices of the stent ('cheese-grating'), reducing the plaque pushed into arterial side branches by the stent (snow-ploughing), reducing the risk of intracranial hyperperfusion injury, providing low shear stress so as to reduce the occurrence of restenosis, and minimising plaque occluding the stent, ultimately reducing morbidity and mortality.

It is also envisaged that the stents according to the invention may comprise a composite structure, for example, Drawn Filled Tube Nitinol (DFT).

It is also envisaged that the stents according to the invention may be coated with graphene.

While the stents according to the invention have been described and illustrated with the axial length of the first and second walls of the first and second end portions being of equal length, it is envisaged that in some embodiments of the invention the axial length of the first and second walls of the first and second end portions of the stents may be different. For example, it is envisaged that the first walls of the first end portions, which would be located at the proximal end of the stenosis may be of axial length shorter than the axial length of the second wall of the second end portion. Alternatively, the axial length of the second wall of the second end portion of the stent may be of axial length shorter than the axial length of the first wall of the first end portion of the stent. In general, in cases where a perforator vessel is located relatively close to either the proximal or distal end of the stenosis, the axial length of the first or second wall of the first or second end portion, as the case may be of the stent may be shorter than the axial length of the other one of the first and second walls of the first and second end portions of the stent, in order to engage the non-diseased part of the artery adjacent the stenosis between the stenosis and the perforator vessel without blocking or covering the perforator vessel. For example, in the case of a perforator vessel being relatively close to a stenosis on the distal end of the stenosis, the second wall of the second end portion of the stent would be of axial length shorter than the axial length of the first wall of the first end portion of the stent, and the axial length of the second wall of the second end portion would be such that the second end portion of the stent would engage the non-diseased part of the artery adjacent the stenosis and between the stenosis and the adjacent perforator vessel.

Therefore, it is envisaged that the axial length of the first and second walls of the first and second end portions of the stents according to the invention may be the same or different.

Additionally, it will be appreciated that the external and internal diameters of the first and second end portions may be different. For example, in a case where the diameters of the vessel at the respective opposite ends of the stenosis are different, the diameters of the first and second end portions would be appropriately selected.

It is also envisaged that the stent 70 described with reference to FIG. 12 when being positioned in the stenosis, instead of the second end portion 4 of the stent being located distally of the perforator 109, the stent may be urged proximally in order to locate the second end portion 4 of the stent between the stenosis and the perforator 109. It is further envisaged that in cases where a perforator 109 is branched from an artery or vessel adjacent a stenosis, either on the proximal or distal end of the stenosis, and there is no space between the stenosis and the branched perforator vessel, it is envisaged that the adjacent one of the first and second end portions of the stent may be located to extend over the perforator vessel 19, and a blood supply would be accommodated through the interstices 20*b* through the corresponding one of the first and second walls of the relevant one of the first and second end portions 3 or 4 of the stent into the perforator vessel 103.

The invention claimed is:

1. A method of treating a stenosis in an intracranial vessel with an intracranial stent, the intracranial stent including a first end portion having a first bore, a second end portion having a second bore, and a central portion extending between the first and second end portions, the central portion being in communication with the first and second bores, the first end portion, the second end portion, and the central portion each forming a plurality of interstices formed by a plurality of struts and crowns, the struts extending continually from the first end portion to the second end portion via the crowns, the method comprising:

locating an expandable intracranial stent within the stenosis of the intracranial vessel, the central portion of the intracranial stent extending through a bore formed by the stenosis and with the first and second end portions adjacent to opposite ends of the stenosis; and expanding the intracranial stent so that the first and second end portions have diameters that are each larger than a diameter of the central portion, and so that the central portion is configured to apply a greater outward force as compared with the first and second end portions due to the interstices of the central portion being smaller than the interstices of the respective first and second end portions.

2. The method of claim 1, wherein the central portion is not axially aligned with the first and/or second end portions when the intracranial stent is expanded in the stenosis.

3. The method of claim 2, wherein the central portion is axially aligned with the first and second end portions when the intracranial stent is in an unexpanded state.

4. The method of claim 1, wherein the central portion is axially aligned with the first and/or second end portions when the intracranial stent is in an expanded state.

5. The method of claim 1, wherein the central portion takes an angled shape together with the first end portion or the second end portion when the intracranial stent is located and expanded in a curved or angled intracranial vessel.

6. The method of claim 1, wherein expanding the intracranial stent includes expanding a pair of transition portions located between the central portion and the first and second end portions, respectively, the stent including radiopaque material that allows visualization of the transition portions.

7. The method of claim 1, wherein expanding the intracranial stent includes expanding a pair of transition portions located between the central portion and the first and second end portions, respectively, the transition portions having interstices that are smaller than interstices of the first and second end portions.

8. The method of claim 1, wherein, after expanding the intracranial stent, the crowns form a V angle of greater than 40 degrees and the crowns in the central portion define a shape of the interstices in the central portion.

9. The method of claim 1, wherein the interstices of the first end portion, the second end portion, and the central portion of the stent each comprise a plurality of struts and wherein at least some of the struts of the central portion are shorter than the struts of the first end portion or of the second end portion.

10. The method of claim 1, wherein the central portion is configured to at least reduce material of the stenosis from penetrating through the interstices thereof.

11. A method of treating a stenosis in an intracranial vessel with an expandable intracranial stent that includes a first end portion having a first bore, a second end portion having a second bore, and a central portion extending between the first and second end portions,
the method comprising:
locating the intracranial stent at the stenosis of the intracranial vessel with the central portion of the intracranial stent being adjacent the stenosis and with the first and second end portions being located adjacent to opposite ends of the stenosis, the locating performed with a microcatheter that is positioned within a bore of the stenosis following location of a guide wire through the bore of the stenosis; and
expanding the intracranial stent so that the first and second end portions have diameters that are each larger than a diameter of the central portion, the first and second end portions and the central portion together forming an annulus that constrains the stenosis between the central portion of the intracranial stent and a wall of the intracranial vessel.

12. The method of claim 11, wherein, after expanding the intracranial stent, a pair of transition portions of the intracranial stent form the annulus together with the first and second end portions and the central portion, the transition portions gradually increasing in diameter away from the central portion towards a respective end portion.

13. The method of claim 11, wherein, after expanding the intracranial stent, the central portion exerts a higher outward radial force than first and second end portions.

14. The method of claim 11, further comprising:
measuring a length of the stenosis; and
based on the measured length, selecting an intracranial stent such that end portions of the intracranial stent extend beyond the stenosis.

15. A method of treating a stenosis in an intracranial vessel with an expandable intracranial stent that includes a first end portion having a first bore, a second end portion having a second bore, and a central portion extending between the first and second end portions, the method comprising:
locating the intracranial stent at the stenosis of the intracranial vessel with the central portion of the intracranial stent being adjacent the stenosis and with the first and second end portions being located adjacent to opposite ends of the stenosis; and expanding the intracranial stent so that the first and second end portions have diameters that are each larger than a diameter of the central portion, the first and second end portions and the central portion together forming an annulus that constrains the stenosis between the central portion of the intracranial stent and a wall of the intracranial vessel, wherein the intracranial stent has a length such that, after the intracranial stent is located and expanded in the intracranial vessel, the intracranial stent prevents the stenosis from blocking a perforator artery adjacent to an end of the stenosis.

16. A method of treating a stenosis in an intracranial vessel with an intracranial stent that includes a first end portion having a first bore, a second end portion having a second bore, and a central portion extending between the first and second end portions, the method comprising:
locating the intracranial stent within the stenosis of the intracranial vessel without use of a balloon catheter to pre-dilate the intracranial vessel, the locating performed with a microcatheter that is positioned within a bore of the stenosis following location of a guide wire through the bore of the stenosis, the central portion of the intracranial stent being located adjacent the stenosis and with the first and second end portions located adjacent to opposite ends of the stenosis; and
expanding the intracranial stent so that the first and second end portions have diameters that are each larger than a diameter of the central portion.

17. The method of claim 16, wherein expanding the intracranial stent is performed by use of outward radial force generated by self- expansion of the central portion of the intracranial stent.

18. The method of claim 16, further comprising:
re-positioning the intracranial stent relative to the stenosis; and
electrolytically severing a structure between a delivery wire and the intracranial stent.

19. The method of claim 16, further comprising:
partially deploying the intracranial stent from the microcatheter;
re-sheathing the intracranial stent;
re-positioning the intracranial stent relative to the stenosis; and
withdrawing the microcatheter and releasing the intracranial stent from the microcatheter and the guide wire.

20. The method of claim 16, wherein the central portion expands to a diameter that is sized to perfuse tissue downstream of the stenosis to an oligemic state.

21. The method of claim 20, wherein the central portion exerts radial outward pressure that at least prevents further narrowing of the stenosis to maintain blood flow.

22. The method of claim 20, wherein the diameter of the central portion is less than the diameter of non-diseased portions of the vessel adjacent to the stenosis.

23. The method of claim 1, wherein the central portion defines a cross-sectional area that, upon expanding the intracranial stent, is smaller than a cross-sectional area of a non-diseased vessel adjacent the stenosis.

24. The method of claim 16, wherein the expandable intracranial stent is expanded within the stenosis without pre-dilation with an angioplasty balloon or without post-dilation with the angioplasty balloon after the intracranial stent is deployed.

25. The method of claim 24, wherein, in the central portion of the intracranial stent, a strut length, a strut width, and a crown inner radius are each sized to generate a radial force upon expansion of the intracranial stent such that the central portion of the intracranial stent dilates the stenosis directly without pre-dilation of the stenosis with an angioplasty balloon or without post-dilation of the stenosis.

26. The method of claim 25, further comprising:

advancing an intracranial guidewire through the bore in the stenosis;

advancing a microcatheter over the guidewire and through the bore of the stenosis;

removing the guidewire;

delivering the intracranial stent through the microcatheter until positioned in the stenosis;

retracting the microcatheter to deploy the intracranial stent and allow the intracranial stent to expand in the stenosis and dilate the stenosis directly; and removing the microcatheter.

27. The method of claim 16, further comprising:

measuring a diameter of a bore of the stenosis of the intracranial vessel; and selecting the intracranial stent based on the diameter of the stenosis of the intracranial stenosis.

28. The method of claim 16, further comprising:

measuring a diameter of the intracranial vessel adjacent the stenosis;

determining a desired diameter of a bore through the stenosis, the desired diameter being less than the diameter of the intracranial vessel adjacent the stenosis; and selecting the intracranial stent from a plurality of intracranial stents such that the central portion, when expanded, dilates the stenosis to approximately the desired diameter.

29. The method of claim 16, further comprising:

re-positioning the intracranial stent relative to the stenosis; and deploying the intracranial stent by fully unsheathing the intracranial stent with a microcatheter.

30. The method of claim 11, wherein the diameter of the central portion is less than the diameter of non-diseased portions of the vessel adjacent to the stenosis.

31. The method of claim 11, wherein the expandable intracranial stent is expanded within the stenosis without pre-dilation with an angioplasty balloon or without post-dilation with the angioplasty balloon after the intracranial stent is deployed.

* * * * *